(12) United States Patent
Hayashi et al.

(10) Patent No.: US 8,782,897 B2
(45) Date of Patent: Jul. 22, 2014

(54) METHOD FOR MANUFACTURING DENTAL IMPLANT

(71) Applicant: Seiko Epson Corporation, Tokyo (JP)

(72) Inventors: Junichi Hayashi, Nagano-ken (JP); Michio Ito, Nagano-ken (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/783,673

(22) Filed: Mar. 4, 2013

(65) Prior Publication Data

US 2013/0177468 A1  Jul. 11, 2013

Related U.S. Application Data

(62) Division of application No. 12/179,842, filed on Jul. 25, 2008, now Pat. No. 8,408,905.

(30) Foreign Application Priority Data

Jul. 27, 2007 (JP) .................................. 2007-196497

(51) Int. Cl.
*A61C 8/00* (2006.01)
*A61C 13/00* (2006.01)

(52) U.S. Cl.
CPC ............ *A61C 8/0075* (2013.01); *A61C 13/0003* (2013.01); *A61C 8/005* (2013.01); *A61C 8/0012* (2013.01)
USPC ............... 29/896.1; 29/447; 29/527.1; 419/6; 433/173

(58) Field of Classification Search
CPC .................................................. A61C 8/0075
USPC ......... 29/896.1, 896.11, 527.1, 447; 419/5, 6, 419/16, 26, 29, 36; 264/16, 17, 219, 642; 433/172–174, 176, 201.1, 202.1, 223
See application file for complete search history.

(56) References Cited

U.S. PATENT DOCUMENTS

| | | | |
|---|---|---|---|
| 3,589,011 A | 6/1971 | Sneer | |
| 3,934,347 A | 1/1976 | Lash et al. | |
| 4,416,629 A | 11/1983 | Mozsary et al. | |
| 4,488,875 A | 12/1984 | Niznick | |
| 4,525,145 A | 6/1985 | Scheicher et al. | |

(Continued)

FOREIGN PATENT DOCUMENTS

| | | |
|---|---|---|
| DE | 4021813 A1 | 1/1992 |
| DE | 4230009 A1 | 4/1993 |

(Continued)

*Primary Examiner* — David Bryant
*Assistant Examiner* — Steven A Maynard

(57) ABSTRACT

A dental implant for preventing elution of metal when applied within an oral cavity and preventing the occurrence of mismatching (bumpy occlusion or the like) when fixed in place, and its manufacturing method are provided. The abutment is manufactured through steps including molding a titanium molded body composition to obtain a titanium molded body, molding a ceramic molded body composition to obtain a ceramic molded body, assembling the titanium molded body and the ceramic molded body together to obtain an assembled body, degreasing the assembled body so that the titanium molded body becomes a titanium degreased body and the ceramic molded body becomes a ceramic degreased body, and sintering the assembled body to transform the titanium degreased body into a titanium member and to transform the ceramic degreased body into a ceramic member so that the titanium member and the ceramic member are firmly fixed and joined together.

11 Claims, 6 Drawing Sheets

(56) References Cited

U.S. PATENT DOCUMENTS

| | | |
|---|---|---|
| 4,657,510 A | 4/1987 | Gittleman |
| 4,713,003 A | 12/1987 | Symington et al. |
| 4,713,004 A | 12/1987 | Linkow et al. |
| 4,722,688 A | 2/1988 | Lonca |
| 4,832,601 A | 5/1989 | Linden |
| 4,854,872 A | 8/1989 | Detsch |
| 5,033,962 A | 7/1991 | Scatena |
| 5,040,982 A | 8/1991 | Stefan-Dogar |
| 5,049,073 A | 9/1991 | Lauks |
| 5,071,350 A | 12/1991 | Niznick |
| 5,087,199 A | 2/1992 | Lazarof |
| 5,116,225 A | 5/1992 | Riera |
| 5,195,891 A | 3/1993 | Sulc |
| 5,213,500 A | 5/1993 | Salazar et al. |
| 5,346,396 A | 9/1994 | Hakamatsuka |
| 5,417,570 A | 5/1995 | Zuest et al. |
| 5,482,463 A | 1/1996 | Wilson, Jr. et al. |
| 5,556,280 A | 9/1996 | Pelak |
| 5,564,921 A | 10/1996 | Marlin |
| 5,599,185 A | 2/1997 | Greenberg |
| 5,678,995 A | 10/1997 | Kirsch et al. |
| 5,685,714 A | 11/1997 | Beaty et al. |
| 5,733,122 A | 3/1998 | Gordon |
| 5,782,918 A | 7/1998 | Klardie et al. |
| 5,810,590 A | 9/1998 | Fried et al. |
| 5,871,358 A | 2/1999 | Ingber et al. |
| 5,888,218 A | 3/1999 | Folsom |
| 5,967,782 A | 10/1999 | Shimodaira et al. |
| 6,012,923 A | 1/2000 | Bassett et al. |
| 6,022,509 A * | 2/2000 | Matthews et al. ............... 419/38 |
| 6,030,219 A | 2/2000 | Zuest et al. |
| 6,068,478 A | 5/2000 | Grande et al. |
| 6,244,867 B1 | 6/2001 | Aravena et al. |
| 6,273,720 B1 | 8/2001 | Spalten |
| 6,461,160 B1 | 10/2002 | Sutter |
| 6,537,487 B1 * | 3/2003 | Kuhns ............................ 419/29 |
| 6,644,969 B2 | 11/2003 | Kumar |
| 6,695,616 B2 | 2/2004 | Ellison |
| 6,733,703 B2 * | 5/2004 | Billiet et al. ................. 264/40.1 |
| 7,674,426 B2 * | 3/2010 | Grohowski, Jr. ................... 419/2 |
| 2001/0037154 A1 | 11/2001 | Martin |
| 2003/0082499 A1 | 5/2003 | Halldin et al. |
| 2004/0234926 A1 | 11/2004 | Halldin et al. |
| 2005/0136378 A1 | 6/2005 | Ennajimi et al. |
| 2005/0181330 A1 | 8/2005 | Kim et al. |
| 2006/0014120 A1 | 1/2006 | Sapian |
| 2010/0062396 A1 | 3/2010 | Hock et al. |
| 2011/0294090 A1 | 12/2011 | Jung |

FOREIGN PATENT DOCUMENTS

| | | |
|---|---|---|
| DE | 19714759 A1 | 10/1998 |
| DE | 202006001796 U1 | 7/2006 |
| DE | 102005042091 A1 | 3/2007 |
| EP | 1570804 A1 | 9/2005 |
| EP | 1939153 | 7/2008 |
| JP | 04-049958 | 2/1992 |
| JP | 05-168651 | 7/1993 |
| JP | 5-228161 | 9/1993 |
| JP | 06-048855 | 2/1994 |
| JP | 06-105899 | 4/1994 |
| JP | 06-125979 | 5/1994 |
| JP | 08-117247 | 5/1996 |
| JP | 08-117324 | 5/1996 |
| JP | 08-310878 | 11/1996 |
| JP | 10033562 A | 2/1998 |
| JP | 11-071186 | 3/1999 |
| JP | 2000-024004 | 1/2000 |
| JP | 2000-087105 | 3/2000 |
| JP | 2003-525685 | 9/2003 |
| JP | 2003-277806 | 10/2003 |
| JP | 2004-313525 | 11/2004 |
| WO | 01/66022 A1 | 9/2001 |
| WO | 2007016796 | 2/2007 |

* cited by examiner

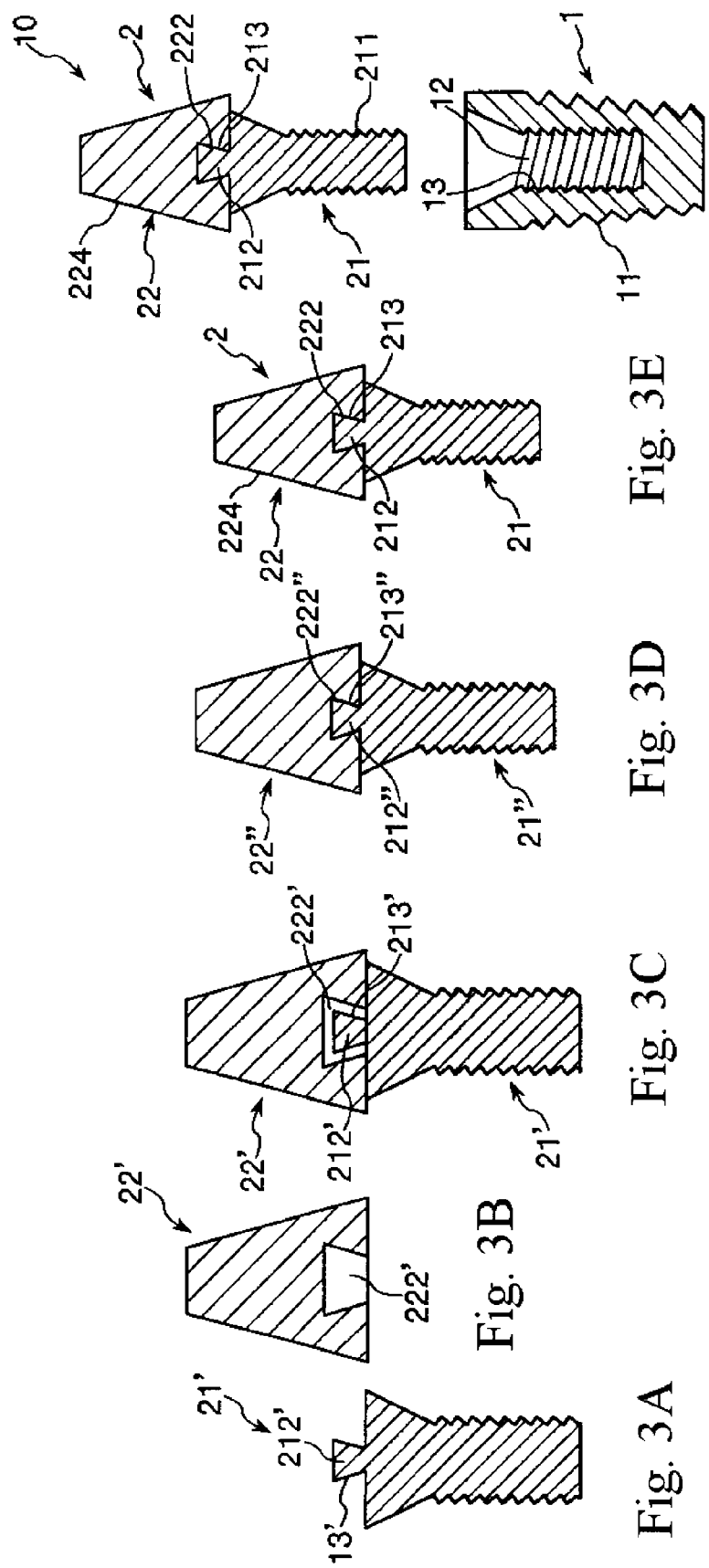

METHOD FOR MANUFACTURING DENTAL IMPLANT

CROSS-REFERENCE TO RELATED APPLICATION

This application is a divisional of, and claims priority on under 35 U.S.C. §120 on, application Ser. No. 12/179,842, filed on Jul. 25, 2008, and claims priority to Japanese Patent Application No. 2007-196497 filed on Jul. 27, 2007 which is hereby expressly incorporated by reference herein in its entirety.

BACKGROUND

1. Technical Field

The present invention relates to a method for manufacturing a dental implant and a dental implant manufactured by the method.

2. Related Art

An implant (dental implant) has been extensively used to restore the function of a tooth lost by various causes. In general, the dental implant includes a fixture anchored to a jawbone and an abutment threadedly coupled to the fixture.

A crown restoration is capped on the dental implant (the abutment threadedly coupled to the fixture) and fixed thereto with dental cement, thereby bringing the dental implant into a shape corresponding to that of an original tooth.

Conventionally, from the standpoint of compatibility to a living body, strength and so forth, titanium or titanium alloy has been generally used as a constituent material of the implant (see, e.g., JP-A-2000-24004, page 3, right column, lines 40 to 42).

Ceramic is generally used as a constituent material of the crown restoration to lessen the difference in appearance between the crown restoration and the tooth of a living body.

A metal portion (metal layer) made of gold alloy or the like is arranged on the inner surface (the implant-side surface) of the crown restoration in an effort to improve occlusion or to reliably prevent occurrence of cracks in the crown restoration.

In other words, a laminated body including a metal portion (metal layer) made of metal and a layer made of ceramic is widely used as the crown restoration.

If the crown restoration has the metal portion as set forth above, however, a galvanic cell is formed between the metal portion and the titanium-made implant. This may possibly cause metal to be eluted into the living body, thereby adversely affecting the living body.

With a view to avoid such a problem, it would be conceivable that the metal portion of the crown restoration is fixed to the implant with a relatively large quantity of dental cement so that they should not make contact with each other.

In this case, it becomes difficult to adjust the height and angle of the crown restoration to be fixed to the implant as designed at the outset. It is also difficult to obtain sufficiently high bonding strength.

In order to prevent contact between the titanium or titanium alloy of which the implant is made and the metal portion of the crown restoration, it would also be conceivable that the titanium or titanium alloy is coated with insulating ceramic.

Ceramic is usually inferior in its bondability with titanium or titanium alloy, although it exhibits superior bondability with gold alloy. This makes it difficult to sufficiently increase the bonding strength between the portion made of titanium or titanium alloy and the portion made of ceramic.

As a result, mismatching (bumpy occlusion or the like) of the implant is apt to occur, consequently deteriorating the feeling of use of the implant.

SUMMARY

It is an object of the present invention to provide a dental implant capable of reliably preventing elution of metal when the dental implant is applied within an oral cavity and capable of reliably preventing occurrence of mismatching (bumpy occlusion or the like) when the dental implant is fixed in place, and a method for manufacturing the dental implant.

With this object in mind, one aspect of the present invention is directed to a method for manufacturing a dental implant including an abutment.

The abutment is manufactured through the steps comprising a titanium molded body production step for molding a titanium molded body composition containing powder composed of titanium or titanium alloy and a binder to obtain a titanium molded body, a ceramic molded body production step for molding a ceramic molded body composition containing powder composed of oxide-based ceramic and a binder to obtain a ceramic molded body, an assembling step for assembling the titanium molded body and the ceramic molded body together to obtain an assembled body, a degreasing step for degreasing the assembled body so that the binder contained in the titanium molded body and the binder contained in the ceramic molded body are removed therefrom to transform the titanium molded body into a titanium degreased body and to transform the ceramic molded body into a ceramic degreased body, and a sintering step for sintering the assembled body thus degreased to transform the titanium degreased body into a titanium member as a sintered body and to transform the ceramic degreased body into a ceramic member as a sintered body so that the titanium member and the ceramic member are firmly fixed and joined together.

The method of the present invention is capable of reliably preventing elution of metal when the dental implant is applied within an oral cavity and capable of reliably preventing occurrence of mismatching when the dental implant is fixed in place.

In the method of the present invention, it is preferred that one of the titanium and ceramic molded bodies has a recess, and the other molded body has a protrusion inserted into the recess, wherein a content percentage of the binder contained in the molded body having the recess is greater than that of the molded body having the protrusion.

This makes it possible to greatly increase adhesion and fixing strength between the titanium member and the ceramic member and to effectively prevent occurrence of mismatching when the dental implant is fixed in place.

In the method of the present invention, it is preferred that the content percentage of the binder contained in the molded body having the protrusion is in the range of 3 to 35 wt %.

This makes it possible to obtain a molded body having a protrusion with increased moldability and to greatly increase adhesion and fixing strength between the titanium member and the ceramic member in the dental implant finally obtained.

Furthermore, it is possible to effectively prevent the molded body having the protrusion from being inadvertently deformed in the degreasing process, which in turn makes it possible to greatly increase dimensional accuracy of the dental implant finally obtained.

In the method of the present invention, it is preferred that the content percentage of the binder contained in the molded body having the recess is in the range of 6 to 40 wt %.

This makes it possible to effectively prevent the molded body having the recess from being inadvertently deformed in the degreasing process and to greatly increase adhesion and fixing strength between the titanium member and the ceramic member in the dental implant finally obtained.

Furthermore, it is possible to obtain a molded body having a recess with increased moldability.

In the method of the present invention, it is preferred that in the case where the content percentage of the binder contained in the molded body having the recess is defined by $C_A$ (wt %) and the content percentage of the binder contained in the molded body having the protrusion is defined by $C_B$ (wt %), $C_A$ and $C_B$ satisfy a relation of $3 \le C_A - C_B \le 15$.

This makes it possible to greatly increase adhesion and fixing strength between the titanium member and the ceramic member in the dental implant finally obtained and to effectively prevent the molded body having the protrusion and the molded body having the recess from being inadvertently deformed in the degreasing process.

As a result, it is possible to greatly enhance mechanical stability and dimensional accuracy of the dental implant finally obtained.

In the method of the present invention, it is preferred that the recess of the molded body has a size lager than that of the protrusion of the molded body, wherein in the assembling step, the assembled body is assembled by inserting the protrusion of the molded body into the recess of the molded body so that a clearance is existed therebetween, and wherein in the degreasing and sintering steps, when the assembled body is degreased and sintered, the molded body having the recess contracts greater than the molded body having the protrusion so that the clearance is eliminated, thereby bringing a protrusion of the member into close contact with and fitting to a recess of the member.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the molded body has a portion whose cross-sectional area is increased toward a dead-end portion of the recess of the molded body in a state that the protrusion of the molded body is inserted into the recess of the molded body.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the molded body has a portion whose cross-sectional area is continuously increased toward a dead-end portion of the recess of the molded body in a state that the protrusion of the molded body is inserted into the recess of the molded body.

This makes it possible to greatly increase adhesion and fixing strength between the titanium member and the ceramic member and to effectively prevent occurrence of mismatching when the dental implant is fixed in place.

In the method of the present invention, it is preferred that the protrusion of the molded body has a portion whose cross-sectional shape is non-circular.

This makes it possible to reliably prevent the titanium member and the ceramic member from making relative rotational movement and to effectively prevent occurrence of mismatching when the dental implant is fixed in place.

In the method of the present invention, it is preferred that the ceramic member is composed of zirconia as a major component thereof.

Among various kinds of oxide-based ceramics, zirconia is particularly superior in living body affinity and strength. If the ceramic member is composed of zirconia as a major component thereof, it becomes possible to remarkably improve safety of the dental implant and also to more reliably prevent occurrence of problems such as gum recession after application of the dental implant. It is also possible to greatly enhance durability of the dental implant.

Further, among various kinds of oxide-based ceramics, zirconia exhibits very low adhesion with titanium or titanium alloy. In a method using an adhesive agent or the like, therefore, adhesion and bonding strength between a member made of titanium or titanium alloy and a member made of zirconia becomes very low.

However, in the present invention, since the titanium member and the ceramic member are firmly fixed and joined together through a sintering process, it is possible to sufficiently increase adhesion and fixing strength between the titanium member and the ceramic member without using any adhesive.

In other words, effects provided by the present invention become more conspicuous if the ceramic member is composed of zirconia as a major component thereof.

In the method of the present invention, it is preferred that the dental implant further includes a fixture to be coupled to the abutment and anchored to a jawbone, the fixture made of titanium or titanium alloy.

This makes it possible to greatly increase fixing strength of the dental implant to a living body (a jawbone) when the dental implant is applied to the living body. It is also possible to greatly increase adhesion between the fixture and the abutment when the dental implant is applied to the living body.

In the method of the present invention, it is preferred that the ceramic member has a contact surface with which a metal having a composition different from that of a constituent material of the titanium member makes contact.

This makes it possible to reliably prevent elution of metal when the dental implant is applied within an oral cavity.

Another aspect of the present invention is directed to a dental implant including an abutment. The dental implant comprises a titanium member composed of a sintered body made from titanium or titanium alloy, and a ceramic member composed of a sintered body made from oxide-based ceramic, wherein the titanium member and the ceramic member are firmly fixed and joined together through a sintering process.

The dental implant of the present invention is capable of reliably preventing elution of metal when the dental implant is applied within an oral cavity and capable of reliably preventing occurrence of mismatching when the dental implant is fixed in place.

In the dental implant of the present invention, it is preferred that one of the titanium member and the ceramic member has a recess and the other of the titanium member and the ceramic member has a protrusion inserted into the recess.

This makes it possible to greatly increase adhesion and fixing strength between the titanium member and the ceramic member and to effectively prevent occurrence of mismatching when the dental implant is fixed in place.

In the dental implant of the present invention, it is preferred that the protrusion of the member is in close contact with and fitted to the recess of the member.

This makes it possible to greatly increase adhesion and fixing strength between the titanium member and the ceramic member and to effectively prevent occurrence of mismatching when the dental implant is fixed in place.

In the dental implant of the present invention, it is preferred that the protrusion of the member has a portion whose cross-sectional area is increased toward a dead-end portion of the recess of the member.

This makes it possible to greatly increase adhesion and fixing strength between the titanium member and the ceramic member and to effectively prevent occurrence of mismatching when the dental implant is fixed in place.

In the dental implant of the present invention, it is preferred that the ceramic member has a contact surface with which a metal member having a composition different from that of a constituent material of the titanium member makes contact.

This makes it possible to reliably prevent elution of metal when the dental implant is applied within an oral cavity.

The above and other objects, features and advantages of the present invention will become apparent from the following description of preferred embodiments given in conjunction with the accompanying drawings.

BRIEF DESCRIPTION OF THE DRAWINGS

FIGS. 3A to 3F are process views illustrating one preferred embodiment of a dental implant manufacturing method in accordance with the present invention.

DESCRIPTION OF EXEMPLARY EMBODIMENTS

Hereinafter, preferred embodiments of the present invention will be described with reference to the accompanying drawings.

Figure 1C:
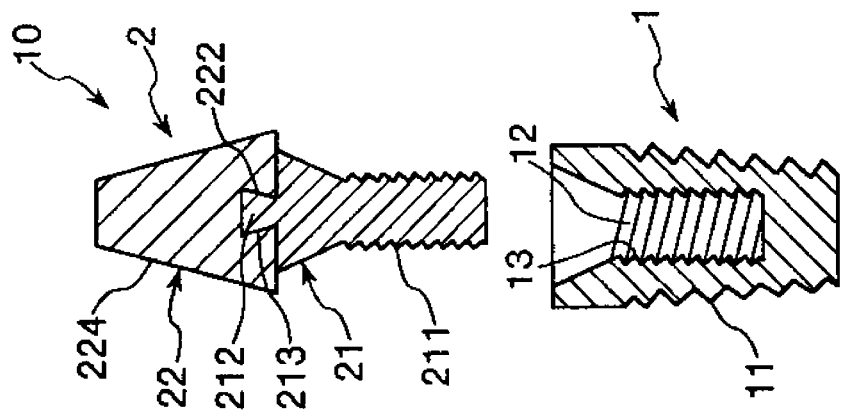
FIG. 1C is a vertical section view showing the preferred embodiment of the dental implant in which the fixture and the abutment are not threadedly coupled.
Figure 1B:
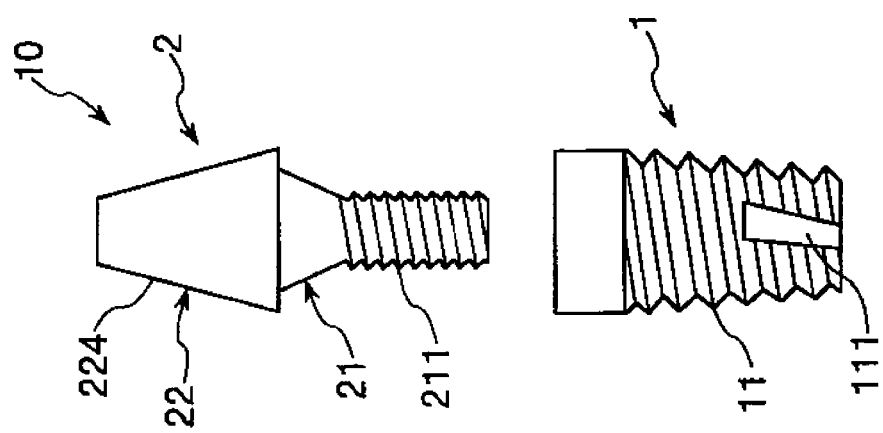
FIG. 1B is a front view showing the preferred embodiment of the dental implant in which the fixture and the abutment are not threadedly coupled.
Figure 1A:
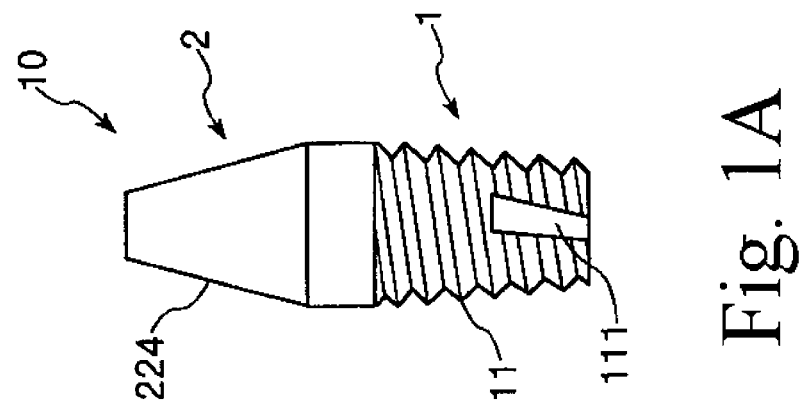
FIG. 1A is a front view showing one preferred embodiment of a dental implant in accordance with the present invention, in which a fixture and an abutment are threadedly coupled.

FIG. 1A is a front view showing one preferred embodiment of a dental implant in accordance with the present invention, in which a fixture and an abutment are threadedly coupled. FIG. 1B is a front view showing the preferred embodiment of the dental implant in which the fixture and the abutment are not threadedly coupled. FIG. 1C is a vertical section view showing the preferred embodiment of the dental implant in which the fixture and the abutment are not threadedly coupled.

Figure 2A:
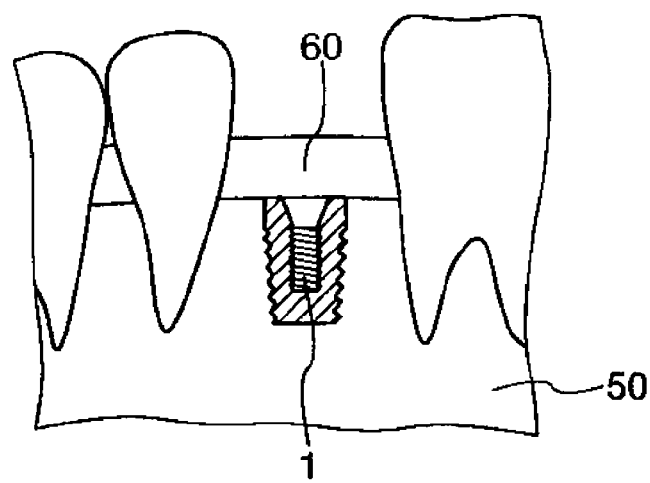
FIGS. 2A to 2C are views for explaining an operation method using the dental implant.
Figure 2B:
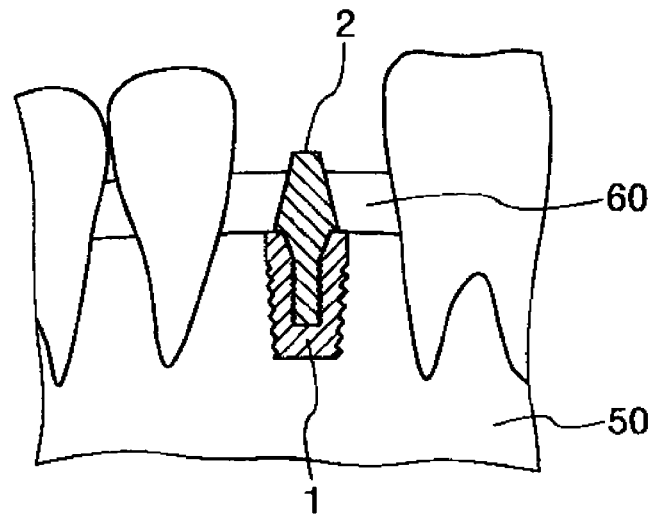
Figure 2C:
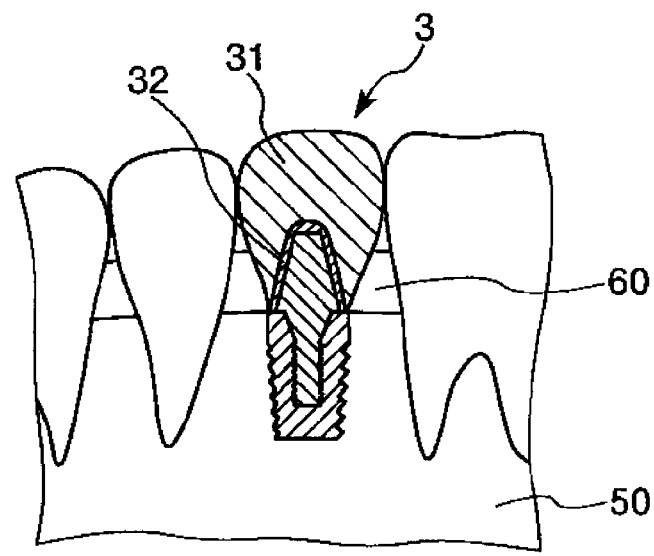

FIGS. 2A to 2C are views for explaining an operation method using the dental implant. FIGS. 3A to 3F are process views illustrating one preferred embodiment of a dental implant manufacturing method in accordance with the present invention.

Figure 4A:
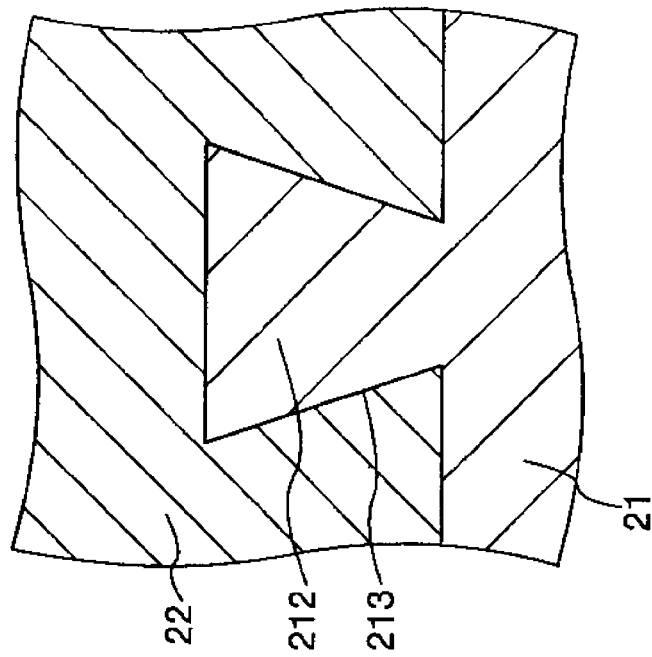
FIG. 4A is a vertical section view showing a boundary portion between a titanium molded body and a ceramic molded body which are kept in an assembled state.
Figure 4B:
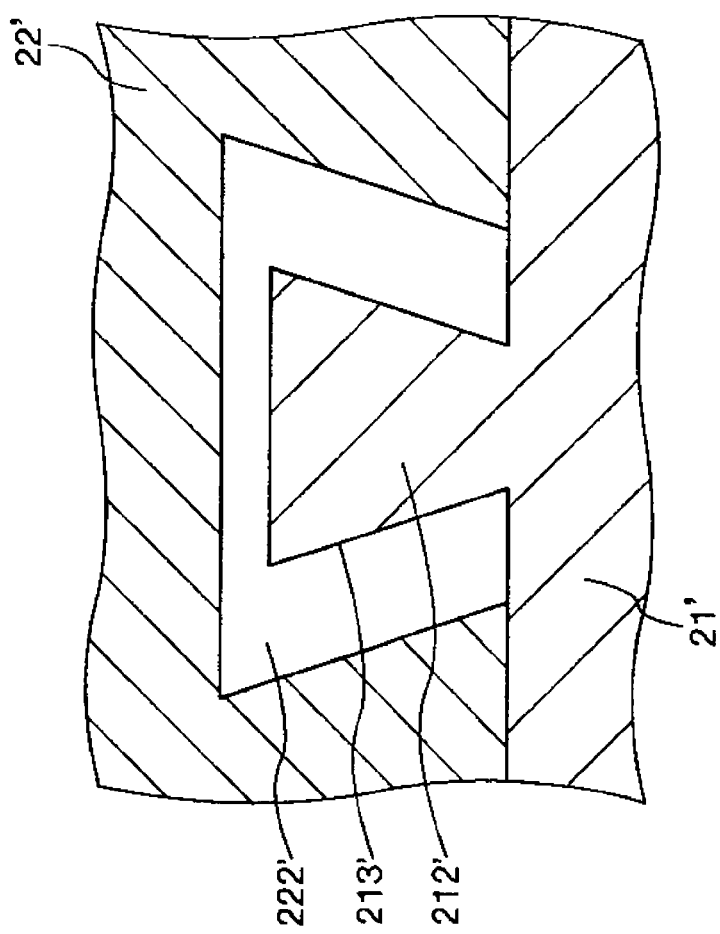
FIG. 4B is a vertical section view showing a boundary portion between a titanium member and a ceramic member after a sintering step has been performed.

FIG. 4A is a vertical section view showing a boundary portion between a titanium molded body and a ceramic molded body which are kept in an assembled state. FIG. 4B is a vertical section view showing a boundary portion between a titanium member and a ceramic member after a sintering step has been performed.

The drawings referred to in this specification show parts of components in an exaggerated state and does not accurately reflect the actual dimension thereof.

Dental Implant

First, description will be made on a dental implant in accordance with the present invention.

A dental implant 10 includes a fixture 1 anchored to a jawbone and an abutment 2 threadedly coupled to the fixture 1.

(1) Fixture

The fixture 1 is a member that will be anchored to the jawbone in an operation using the dental implant 10. The fixture 1 is formed into a bottom-closed tubular shape. A male thread portion 11 is provided on an outer circumferential surface of the fixture 1. This makes it possible to threadedly anchor the fixture 1 to the jawbone in which a thread is formed by cutting or other methods.

A cutout portion 111 having a specified length is formed in a part of the male thread portion 11 to extend in an axial direction of the fixture 1. No spiral groove is formed in the cutout portion 111. This makes it possible to threadedly anchor the fixture 1 to the jawbone in an easy and reliable manner during a course of conducting an operation.

After the operation comes to an end, osteogenesis is progressed by osteoblastic cells in a region of a living body corresponding to the cutout portion 111. Therefore, it is possible to effectively prevent the thread coupling from being loosened.

The fixture 1 has a tubular portion 12 into which the abutment 2 is inserted as mentioned below. Formed on an inner circumferential surface of the fixture 1 is a female thread portion 13 that can make thread coupling with a male thread portion 211 of the abutment 2 (a titanium member 21).

The fixture 1 may be made of any material. From the standpoint of living body compatibility, strength and so forth, it is preferred that the fixture 1 is made of titanium or titanium alloy.

(2) Abutment

The abutment 2 is a member that will be fixed to the fixture 1 in the operation using the dental implant 10. Further, the abutment 2 is capped by a crown restoration 3 which is used for a purpose of improving aesthetic appearance and assuring enhanced occlusion.

The abutment 2 includes a titanium member 21 made of titanium or titanium alloy and a ceramic member 22 made of oxide-based ceramic.

(2.1) Titanium Member

The titanium member 21 is one of constituent members of the abutment 2 that will be threadedly coupled to the female thread portion 13 of the fixture 1 as mentioned above. The titanium member 21 has a male thread portion 211 threadedly coupled to the female thread portion 13 of the fixture 1.

The titanium member 21 is made of titanium or titanium alloy. It is preferred that the titanium member 21 is made of a material having the same composition as that of a constituent material of the fixture 1. This makes it possible to greatly improve adhesion between the fixture 1 and the abutment 2.

Furthermore, this makes it possible to reliably prevent occurrence of problems such as elution of metal within an oral cavity due to a galvanic cell formed by an electric potential difference between the constituent material of the fixture 1 and the constituent material of the abutment 2.

In the illustrated configuration, the titanium member has a protrusion 212 to which a recess 222 formed in the ceramic member 22 is to be fitted as mentioned below. The protrusion 212 is of a shape complementary to the recess 222 of the ceramic member 22.

The titanium member 21 is firmly fixed and joined to the ceramic member 22 through a joint (engagement) between the protrusion 212 and the recess 222. For this reason, the titanium member 21 and the ceramic member 22 exhibit extremely superior adhesion between them.

The protrusion 212 has a cross-sectional area increasing portion 213 whose cross-sectional area is increased from a base end toward a distal end of the protrusion 212, that is, toward a dead-end portion of the recess 222 of the ceramic member 22.

Provision of the cross-sectional area increasing portion 213 makes it possible to greatly enhance adhesion and fixing strength (joint strength) between the titanium member 21 and the ceramic member 22. It is also possible to more effectively prevent any mismatching (bumpy occlusion or the like) when the dental implant 10 is fixed in place.

Although the cross-sectional area increasing portion 213 may be formed in such a manner that the cross-sectional area of the protrusion 212 is increased either continuously or non-continuously toward the distal end thereof, it is preferred that the cross-sectional area is increased continuously as shown in the drawings.

This makes it possible to greatly enhance adhesion and fixing strength between the titanium member 21 and the ceramic member 22. It is also possible to more effectively prevent any mismatching when the dental implant 10 is fixed in place.

An angle $\theta$ between a surface (a circumferential surface) of the cross-sectional area increasing portion 213 and a heightwise axis of the protrusion 212 is not particularly limited to a specific value, but is preferably in the range of 0.3 to 5°, and more preferably in the range of 1 to 4°.

By setting the angle $\theta$ within the above ranges, the ceramic member 22 is prevented from becoming extremely thin in a region around the recess 222 of the ceramic member 22. As a result, an effect provided by the cross-sectional area increasing portion 213 grows conspicuous.

In other words, it is possible to greatly enhance adhesion and fixing strength between the titanium member 21 and the ceramic member 22 while keeping strength of the ceramic member 22 sufficiently high. As a consequence, it is possible to keep durability of the dental implant 10 sufficiently high and also to more effectively prevent any mismatching when the dental implant 10 is fixed in place.

In contrast, if the angle $\theta$ is smaller than the lower limit value noted above, there is a possibility that the effect provided by the cross-sectional area increasing portion 213 may not be sufficiently attained.

On the other hand, if the angle $\theta$ exceeds the upper limit value noted above, there is a possibility that the ceramic member 22 may have a region with no sufficiently great thickness (a thin region) around the recess 222 to which the protrusion 212 of the titanium member 21 is fitted. This may reduce strength and durability of the dental implant 10.

In the illustrated configuration, the cross-sectional area increasing portion 213 is formed over a full heightwise length of the protrusion 212. This makes it possible to greatly enhance adhesion and fixing strength between the titanium member and the ceramic member 22. It is also possible to more effectively prevent any mismatching when the dental implant 10 is fixed in place.

Furthermore, it is preferred that the protrusion 212 has a portion whose cross-sectional shape is non-circular. This makes it possible to more reliably prevent the titanium member and the ceramic member 22 from making relative rotational movement. It is also possible to more effectively prevent any mismatching when the dental implant 10 is fixed in place.

In this regard, examples of the non-circular shape include a generally polygonal shape such as a triangular shape, a rectangular shape, a hexagonal shape or the like, a partially cutaway circular shape, an elliptical shape and so forth.

A height of the protrusion 212 is not particularly limited to a specific value, but is preferably in the range of 2 to 5 mm, and more preferably in the range of 3 to 4 mm. This makes it possible to greatly increase strength and durability of the abutment 2.

(2.2) Ceramic Member

The ceramic member 22 is a member capped by a crown restoration 3 as mentioned below. In the illustrated configuration, the ceramic member 22 has a recess 222 fitted to the titanium member 21 as mentioned above.

The recess 222 is of a shape complementary to the protrusion 212 of the titanium member 21, thereby keeping adhesion between the titanium member 21 and the ceramic member 22 extremely high.

The ceramic member 22 has a metal bonding surface (a contact surface) 224 that makes contact with a metal portion 32 of the crown restoration 3 when the dental implant 10 is capped by the crown restoration 3 as mentioned below. As set forth above, the ceramic member 22 is made of oxide-based ceramic.

Among various kinds of materials (especially, various kinds of ceramic materials), the oxide-based ceramic is particularly superior in living body compatibility and extremely low in living body hazard. Furthermore, the oxide-based ceramic seldom gathers contaminants and exhibits increased hardness and strength.

Examples of the oxide-based ceramic of which the ceramic member 22 is made include zirconia (zirconium oxide), silicon oxide (silica), aluminum oxide (alumina), calcium oxide, sodium oxide, potassium oxide, boron oxide, zinc oxide, magnesium oxide (magnesia), lithium oxide, tin oxide, indium oxide and titanium oxide, one or more of which may be used independently or in combination.

Among them, it is preferred that the ceramic member 22 is composed of zirconia as a major component thereof. Among various kinds of oxide-based ceramics, zirconia is particularly superior in living body affinity and strength.

If the ceramic member 22 is composed of zirconia as a major component thereof, it becomes possible to remarkably improve safety of the dental implant 10 and also to more reliably prevent occurrence of problems such as gum recession and the like after application of the dental implant 10. It is also possible to greatly enhance durability of the dental implant 10.

Further, among various kinds of oxide-based ceramics, zirconia exhibits very low adhesion with titanium or titanium alloy. In a method using an adhesive agent or the like, therefore, adhesion and bonding strength between a member made of titanium or titanium alloy and a member composed of zirconia becomes very low.

However, in the present invention, since the titanium member and the ceramic member are firmly fixed and joined together through a sintering process, it is possible to sufficiently increase adhesion and fixing strength between the titanium member and the ceramic member without using any adhesive.

In other words, effects provided by the present invention become more conspicuous if the ceramic member is composed of zirconia as a major component thereof.

In this regard, it is to be noted that the term "as a major component thereof" used herein means that a particular component of a material constituting a subject member or composition has the greatest content.

A content of the component is not particularly limited to a specific value, but is preferably 50 wt % or more, more preferably 55 wt % or more, and even more preferably 60 wt % or more of the material constituting the subject member or composition.

Operation Method Using Dental Implant

Next, an operation method using the dental implant 10 will be described with reference to FIGS. 2A to 2C.

Embedding Fixture

After putting a patient under anesthesia, the fixture 1 is threadedly anchored to a jawbone 50 in which a thread is cut in advance (see FIG. 2A). Then, the fixture 1 is covered with a gum 60 if necessary.

Threadedly Coupling Abutment

If osteogenesis is adequately progressed by osteoblastic cells and osteointegration between the fixture 1 and the jawbone 50 is progressed sufficiently after the lapse of a specified time period (usually about 3 to 6 months) from the fixture embedding time, the abutment 2 is threadedly coupled to the fixture 1 anchored to the jawbone 50 (see FIG. 2B).

In the case where the fixture 1 is covered with the gum 60, the fixture 1 is exposed as appropriate by incising the gum 60 prior to threadedly coupling the abutment 2.

Capping Crown Restoration

Next, the crown restoration 3 molded by modeling is fixed to the ceramic member 22 of the abutment 2 (see FIG. 2C). The crown restoration 3 includes a ceramic portion 31 made of ceramic and visually recognized from the outside after performing this operation, and a metal portion 32 made of a metallic material and provided on an inner surface of the ceramic portion 31.

The crown restoration 3 of this configuration exhibits good appearance at the end of the operation and is capable of improving occlusion and reliably preventing occurrence of a crack or other defects in the crown restoration 3.

Examples of the ceramic of which the ceramic portion 31 is made include silicon oxide (silica), aluminum oxide (alumina), calcium oxide, sodium oxide, potassium oxide, boron oxide, zinc oxide, magnesium oxide (magnesia), lithium oxide, tin oxide, indium oxide and titanium oxide.

On the other hand, the metallic material of which the metal portion 32 is made has a composition different from that of the constituent material of the titanium member 21. In general, gold or gold alloy is used as the metallic material.

If the metal portion 32 is made of gold or gold alloy, effects of improving occlusion and preventing occurrence of a crack or other defects in the crown restoration 3 become more conspicuous.

The crown restoration 3 is capped on the abutment 2 so that the metal portion 32 makes contact with the metal bonding surface 224 of the ceramic member 22. Although the metal portion 32 comes into contact with the ceramic member 22 (the metal bonding surface 224) at this time, it does not make contact with the titanium member 21 and the fixture 1. If desired, it may be possible to use dental cement in bonding the abutment 2 and the crown restoration 3 together.

In the case where the gum 60 is incised during the abutment coupling process, it is general that this process of capping the crown restoration 3 is not performed until disappearance of tumescence of the gum 60 is confirmed over a time period of about 1 to 6 weeks after the abutment coupling process.

Dental Implant Manufacturing Method

Next, description will be made on a method for manufacturing the dental implant 10 set forth above.

Titanium Molded Body Production Step

First, a titanium molded body 21' is obtained by molding a titanium molded body composition that contains powder composed of titanium or titanium alloy and a binder (see FIG. 3A). In the present embodiment, the titanium molded body 21' is formed to have a protrusion 212'.

Hereinafter, the titanium molded body composition will be described in detail.

Powder

An average particle size of powder (metal powder) of which the titanium molded body composition is composed is not particularly limited to a specific value, but is preferably in the range of 0.3 to 100 μm, and more preferably in the range of 0.5 to 50 μm.

If the average particle size of the powder falls within the range noted above, it becomes possible to produce the titanium molded body 21' and the titanium member (sintered body) with increased moldability (ease of molding), wherein the titanium member 21 is produced by degreasing and sintering the titanium molded body 21'.

It is also possible to increase density of the titanium member 21 thus obtained and to improve properties of the sintered body such as mechanical strength, dimensional accuracy and the like.

In contrast, if the average particle size of the powder is smaller than the lower limit value noted above, moldability of the titanium molded body 21' exhibits a decrease. If the average particle size of the powder exceeds the upper limit value noted above, it is difficult to sufficiently increase density of the titanium member 21, which may possibly lead to deterioration in properties of the titanium member 21.

The term "average particle size" used herein refers to a particle size of powder distributed at a point of 50% in terms of an accumulated volume in a particle size distribution of subject powder.

Although the power may be produced by any method, it is possible to use powder obtained by, e.g., various kinds of atomizing methods including a liquid atomizing method such as a water-atomizing method or the like (e.g., a fast-rotating water stream atomizing method and a rotating-liquid atomizing method) and a gas atomizing method, a pulverizing method, a hydrogenation method and a hydrogenation-dehydrogenation method.

A content percentage of the powder contained in the titanium molded body composition used in producing the titanium molded body 21' having the protrusion 212' (a content percentage of the powder contained in the titanium molded body 21') is not particularly limited to a specific value.

It is preferred that the content percentage of the powder contained in the titanium molded body composition is greater than a content percentage of powder contained in a ceramic molded body composition (a ceramic molded body composition used in producing a ceramic molded body 22' having a recess 222') as mentioned below, that is, a content percentage of powder contained in the ceramic molded body 22'.

This ensures that a content percentage of the binder contained in the titanium molded body composition (the titanium molded body 21') is kept relatively small and further that the content percentage of the binder contained in the titanium molded body composition (the titanium molded body 21') is smaller than a content percentage of a binder contained in the ceramic molded body composition.

Therefore, it is possible to control shrinkage of molded bodies in a degreasing step mentioned below, and to control shrinkage of degreased bodies in a sintering step mentioned below, so that the shrinkage (contraction) of the titanium molded body 21' can become smaller than that of the ceramic molded body 22'.

In other words, in the degreasing and sintering steps, when the molded bodies (an assembled body which will be described below) are degreased and sintered, the ceramic molded body 22' (the molded body having the recess) can contract greater than the titanium molded body 21' (the molded body having the protrusion).

As a result, it is possible to greatly increase adhesion and fixing strength between the titanium member 21 (having the protrusion 212) and the ceramic member 22 (having the recess 222) of the abutment 2 finally obtained.

The concrete value of the content percentage of the powder contained in the titanium molded body composition (the titanium molded body 21') is preferably in the range of 65 to 97 wt %, and more preferably in the range of 68 to 95 wt %.

If the content percentage of the powder is smaller than the lower limit value noted above, it is likely that the titanium member 21 obtained exhibits reduction in its mechanical strength and dimensional stability. Furthermore, it may possibly become difficult to sufficiently increase fixing strength of the titanium member 21 relative to the ceramic member 22 in the abutment 2 finally obtained.

In contrast, if the content percentage of the powder exceeds the upper limit value noted above, the content percentage of the below-mentioned binder is reduced correspondingly. Thus, the titanium molded body composition exhibits reduced flowability during the molding process, which may possibly reduce operability.

Binder

The binder is a component that heavily affects moldability (ease of molding) of the titanium molded body composition and stability in shape (shape-keeping ability) of the titanium molded body 21' and a titanium degreased body 21" which is obtained by degreasing the titanium molded body 21' as mentioned below.

If the titanium molded body composition contains such a component, it becomes possible to easily and reliably produce the titanium member 21 as a sintered body with increased dimensional accuracy.

Examples of the binder include: various kinds of resin such as polyolefin (e.g., polyethylene, polypropylene and ethylene-vinyl acetate copolymer), acrylic resin (e.g., polymethylmethacrylate and polybuthylmethacrylate), styrene-based resin (e.g., polystyrene), polyvinyl chloride, polyvinylidene chloride, polyamide, polyester (e.g., polyethylene terephthalate and polybutylene terephthalate), polyether, polyvinyl alcohol, polypropylene carbonate or copolymer thereof; various kinds of wax; paraffin; higher fatty acid (e.g., stearic acid); higher alcohol; higher fatty acid ester; higher fatty acid amide; and the like. One or more of these substances may be used independently or in combination.

A content percentage of the binder contained in the titanium molded body composition used in producing the titanium molded body 21' having the protrusion 212' (a content percentage of the binder contained in the titanium molded body 21') is not particularly limited to a specific value.

It is preferred that the content percentage of the binder contained in the titanium molded body composition is smaller than a content percentage of a binder contained in a ceramic molded body composition (a ceramic molded body composition used in producing a ceramic molded body 22' having the recess 222') as mentioned below, that is, a content percentage of a binder contained in the ceramic molded body 22'.

This makes it possible to control shrinkage of molded bodies (degreased bodies) in a sintering step mentioned below, so that the shrinkage of the titanium molded body 21' can become smaller than that of the ceramic molded body 22'.

As a result, it is possible to greatly increase adhesion and fixing strength between the titanium member 21 (having the protrusion 212) and the ceramic member 22 (having the recess 222) of the abutment 2 finally obtained.

The concrete value of the content percentage of the binder contained in the titanium molded body composition is preferably in the range of 3 to 35 wt %, and more preferably in the range of 5 to 32 wt %.

If the content percentage of the binder is smaller than the lower limit value noted above, it is likely that the titanium molded body composition exhibits reduced flowability during the molding process, which may possibly reduce operability.

In contrast, if the content percentage of the binder exceeds the upper limit value noted above, there is a possibility that the titanium member 21 obtained exhibits reduction in its mechanical strength and dimensional stability. Furthermore, it may possibly become difficult to sufficiently increase fixing strength of the titanium member 21 relative to the ceramic member 22 in the abutment 2 finally obtained.

Other Components

Other components may be contained in the titanium molded body composition in addition to the above-mentioned components. Examples of such components include a dispersant (lubricant), a plasticizer and an antioxidant, one or more of which may be used independently or in combination. This allows the titanium molded body composition to exhibit functions inherent in the respective components.

If the titanium molded body composition contains the dispersant among these components, the dispersant adheres to the powder. This makes it possible to improve dispersibility of the powder in the titanium molded body composition.

Consequently, the titanium degreased body 21" and the titanium sintered body (titanium member 21) to be obtained in subsequent steps exhibit particularly high uniform composition (constitution) and property in each and every portion thereof.

If the titanium molded body composition contains the dispersant, it is also possible to greatly improve flowability of the titanium molded body composition when molding the titanium molded body 21' and to increase mold-filling ability thereof. This makes it possible to more reliably obtain a titanium molded body 21' having uniform density.

Examples of the dispersant include: an anionic organic dispersant such as higher fatty acid (e.g., stearic acid, distearic acid, tristearic acid, linolenic acid, octanoic acid, oleic acid, palmitic acid and naphthenic acid), polyacrylic acid, polymethacrylic acid, polymaleic acid, acrylic acid-maleic acid copolymer or polystyrene sulfonic acid; a cationic organic dispersant such as quaternary ammonium acid; a non-ionic organic dispersant such as polyvinyl alcohol, carboxymethyl cellulose or polyethylene glycol; an inorganic dispersant such as tricalcium phosphate; and the like.

Among the above-noted substances, it is preferred that the dispersant is composed of the higher fatty acid as a major component thereof. This is because the higher fatty acid exhibits particularly high powder dispersibility.

Furthermore, a carbon number of the higher fatty acid is preferably in the range of 16 to 30, and more preferably in the range of 16 to 24. If the carbon number of the higher fatty acid falls within the above range, the titanium molded body composition exhibits improved shape-keeping ability with no reduction in moldability.

Additionally, if the carbon number of the higher fatty acid falls within the above range, the higher fatty acid can be easily decomposed at a relatively low temperature.

If the titanium molded body composition contains the plasticizer, it becomes possible to greatly improve plasticity and moldability of the titanium molded body composition. As a result, it is possible to increase mold-filling ability and to more reliably obtain a titanium molded body 21' having uniform density.

Examples of the plasticizer include phthalic acid ester (e.g., DOP, DEP and DBP), adipic acid ester, trimellitic acid ester, sebacic acid ester and the like.

The antioxidant has a function of preventing oxidation of resin of which the binder is composed. Examples of the antioxidant include a hindered phenol-based antioxidant, hydrazine-based antioxidant, and the like.

The titanium molded body composition containing the respective components set forth above can be prepared by, e.g., mixing various kinds of powder corresponding to the components.

If desired, kneading may be performed after the various kinds of powder are mixed. This makes it possible to increase flowability of the titanium molded body composition and to improve homogeneity thereof.

Therefore, it is possible to obtain a titanium molded body 21' having higher density and sufficient homogeneity. As a result, dimensional accuracy of the titanium degreased body 21" and the titanium sintered body (the titanium member 21) can be improved.

The kneading of the mixture can be performed by various kinds of kneading machines such as a pressure type or dual-arm kneader type kneading machine, a roller type kneading machine, a Banbury type kneading machine, and a single-axis or dual-axis extruding machine.

Kneading conditions depend on the particle size of the powder used, the composition of the binder, the blending quantity of the powder and the binder and so forth. As an example, the kneading condition can be set to a condition in that a kneading temperature is in the range of 50 to 200° C. and a kneading time is in the range of 15 to 210 minutes.

If necessary, a kneaded product (compound) obtained is pulverized into pellets (small masses). A diameter of pellets may be set to the range of about 1 to 10 mm. A pulverizing device such as a pelletizer or the like can be used in pelletizing the kneaded product.

The titanium molded body 21' (a non-sintered body of the titanium member 21) is obtained by molding the titanium molded body composition through use of a required molding method. Although the molding method of the titanium molded body 21' is not particularly limited to a specific method, an injection molding method is generally used because the titanium molded body 21' to be molded has a small size and a complex shape.

At the end of the injection molding process, the molded body thus obtained may be subjected to machining, electric discharging, laser processing, etching and so forth in order to remove burrs or to form a minute structure such as a groove or the like.

The molded body obtained by use of the titanium molded body composition contains the binder in a relatively high content percentage. Therefore, the molded body is easier to process than the titanium degreased body 21" and the titanium sintered body (the titanium member 21) which will be set forth below. This means that the molded body can be easily subjected to the above processing.

The titanium molded body 21' obtained in this step has a protrusion 212' with a shape corresponding to that of the protrusion 212 of the titanium member 21. Just like the protrusion 212 described earlier, it is preferred that the protrusion 212' of the titanium molded body 21' has a portion whose cross-sectional shape is non-circular.

This makes it possible to more reliably prevent the titanium member 21 and the ceramic member 22 of the finally obtained abutment 2 from making relative rotational movement. It is also possible to more effectively prevent any mismatching when the dental implant 10 is fixed in place.

Furthermore, the titanium molded body 21' has a cross-sectional area increasing portion 213' (with a cross-sectional area increasing from a base end toward a distal end thereof) that corresponds in shape to the cross-sectional area increasing portion 213 of the titanium member 21.

It is preferred that the cross-sectional area increasing portion 213' should satisfy the same conditions as applied to the cross-sectional area increasing portion 213 set forth earlier.

In other words, although the cross-sectional area increasing portion 213' may be formed in such a manner that the cross-sectional area of the protrusion 212' is increased either continuously or non-continuously toward the distal end thereof, it is preferred that the cross-sectional area is increased continuously.

An angle θ between a surface (a circumferential surface) of the cross-sectional area increasing portion 213' and a heightwise axis of the protrusion 212' is not particularly limited to a specific value, but is preferably in the range of 0.3 to 5°, and more preferably in the range of 1 to 4°.

Moreover, it is preferred that the cross-sectional area increasing portion 213' is formed over a full heightwise length of the protrusion 212'.

Ceramic Molded Body Production Step

A ceramic molded body 22' is obtained by molding a ceramic molded body composition that contains powder composed of oxide-based ceramic and a binder (see FIG. 3B). In the present embodiment, the ceramic molded body 22' is formed to have a recess 222'.

Hereinafter, the ceramic molded body composition will be described in detail.

Powder

An average particle size of powder (oxide-based ceramic powder) of which the ceramic molded body composition is composed is not particularly limited to a specific value, but is preferably in the range of 0.3 to 100 μm, and more preferably in the range of 0.5 to 50 μm.

If the average particle size of the powder falls within the range noted above, it becomes possible to produce the ceramic molded body 22' and the ceramic member (sintered body) with increased moldability (ease of molding), wherein the ceramic member 22 is produced by degreasing and sintering the ceramic molded body 22'.

It is also possible to increase density of the ceramic member 22 thus obtained and to improve properties of the sintered body such as mechanical strength, dimensional accuracy and the like.

In contrast, if the average particle size of the powder is smaller than the lower limit value noted above, moldability of the ceramic molded body 22' exhibits a decrease. If the average particle size of the powder exceeds the upper limit value noted above, it is difficult to sufficiently increase density of the ceramic member 22, which may possibly lead to deterioration in properties of the ceramic member 22.

Although such powder may be produced by any method, it is possible to use powder obtained by, e.g., a gas-phase reaction method, a pulverizing method, a co-precipitation method, a hydrolysis control method, an emulsion method and a sol-gel method.

A content percentage of the powder contained in the ceramic molded body composition used in producing the ceramic molded body 22' having a recess 222' (a content percentage of the powder contained in the ceramic molded body 22') is not particularly limited to a specific value.

It is preferred that the content percentage of the powder contained in the ceramic molded body composition is smaller than the content percentage of the powder contained in the above-mentioned titanium molded body composition (the titanium molded body composition used in producing the titanium molded body 21' having the protrusion 212'), that is, the content percentage of the powder contained in the titanium molded body 21'.

This ensures that the content percentage of the binder contained in the ceramic molded body composition (the ceramic molded body 22') is kept relatively high and further that the content percentage of the binder contained in the ceramic molded body composition (the ceramic molded body 22') is greater than the content percentage of the binder contained in the titanium molded body composition (the titanium molded body 21').

Therefore, it is possible to control shrinkage of molded bodies (degreased bodies) in a sintering step mentioned below, so that the shrinkage of the ceramic molded body 22' can become greater than that of the titanium molded body 21'.

As a result, it is possible to sufficiently improve dimensional accuracy of the abutment 2 finally obtained and to greatly increase adhesion and fixing strength between the titanium member 21 (having the protrusion 212) and the ceramic member 22 (having the recess 222).

The concrete value of the content percentage of the powder contained in the ceramic molded body composition (the ceramic molded body 22') is in the range of preferably 60 to 94 wt %, and more preferably in the range of 65 to 92 wt %.

If the content percentage of the powder is smaller than the lower limit value noted above, it is likely that the ceramic member 22 obtained exhibits reduction in its mechanical strength and dimensional stability.

In contrast, if the content percentage of the powder exceeds the upper limit value noted above, the content percentage of the below-mentioned binder is reduced correspondingly. Thus, the ceramic molded body composition exhibits reduced flowability during the molding process, which may possibly reduce operability.

Furthermore, it may possibly become difficult to sufficiently increase fixing strength of the ceramic member 22 relative to the titanium member 21 in the abutment 2 finally obtained.

Binder

The binder is a component that heavily affects moldability (ease of molding) of the ceramic molded body composition and stability in shape (shape-keeping ability) of the ceramic molded body 22' and a ceramic degreased body 22" which is obtained by degreasing the ceramic molded body 22' as mentioned below.

If the ceramic molded body composition contains such a component, it becomes possible to easily and reliably produce the ceramic member 22 as a sintered body with increased dimensional accuracy.

As the binder of the ceramic molded body composition, it is possible to use the substances cited above as examples of the binder of the titanium molded body composition.

A content percentage of the binder contained in the ceramic molded body composition used in producing the ceramic molded body 22' having the recess 222' (a content percentage of the binder contained in the ceramic molded body 22') is not particularly limited to a specific value.

It is preferred that the content percentage of the binder contained in the ceramic molded body composition is greater than the content percentage of the binder contained in the above-mentioned titanium molded body composition (the titanium molded body composition used in producing the titanium molded body 21' having the protrusion 212'), that is, the content percentage of the binder contained in the titanium molded body 21'.

This makes it possible to control shrinkage of molded bodies (degreased bodies) in a sintering step mentioned below, so that the shrinkage of the titanium molded body 21' can become smaller than that of the ceramic molded body 22'.

As a result, it is possible to greatly increase adhesion and fixing strength between the titanium member 21 (having the protrusion 212) and the ceramic member 22 (having the recess 222) of the abutment 2 finally obtained.

The content percentage of the binder contained in the ceramic molded body composition (the ceramic molded body 22') is preferably in the range of 6 to 40 wt %, and more preferably in the range of 8 to 35 wt %.

If the content percentage of the binder is smaller than the lower limit value noted above, it is likely that the ceramic molded body composition exhibits reduced flowability during the molding process, which may possibly reduce operability.

Furthermore, it may possibly become difficult to sufficiently increase fixing strength of the ceramic member 22 relative to the titanium member 21 in the abutment 2 finally obtained.

In contrast, if the content percentage of the binder exceeds the upper limit value noted above, there is a possibility that the ceramic member 22 obtained exhibits reduction in its mechanical strength and dimensional stability.

In this regard, in the case where the content percentage of the binder contained in the ceramic molded body 22' (the molded body having the recess) is defined by $C_A$ (wt %) and the content percentage of the binder contained in the titanium molded body 21' (the molded body with the protrusion) is defined by $C_B$ (wt %), $C_A$ and $C_B$ satisfy preferably a relation of $3 \leq C_A - C_B \leq 15$, and more preferably a relation of $4 \leq C_A - C_B \leq 12$.

If the $C_A$ and $C_B$ satisfy the above relation, the ceramic molded body 22' can contract sufficiently greater than the titanium molded body 21'. Therefore, it becomes possible to greatly increase adhesion and fixing strength between the titanium member 21 and the ceramic member 22 in the dental implant 10 finally obtained.

Further, it is also possible to effectively prevent the titanium molded body 21' and the ceramic molded body 22' from undergoing inadvertent deformation in the degreasing process. As a result, it is possible to greatly improve mechanical stability and dimensional accuracy of the dental implant 10 finally obtained.

Other Components

Other components may be contained in the ceramic molded body composition in addition to the above-mentioned components. As these components, it is possible to use the substances cited above as examples of the components of the titanium molded body composition. The same effects as described above can be obtained by doing so.

The ceramic molded body composition containing the respective components set forth above can be prepared by, e.g., mixing various kinds of powder corresponding to the components.

If desired, kneading may be performed after the various kinds of powder are mixed. This makes it possible to increase flowability of the ceramic molded body composition and to improve homogeneity of the composition.

Therefore, it is possible to increase density and homogeneity of the ceramic molded body 22' and to improve dimensional accuracy of the ceramic molded body 22' and the ceramic sintered body (the ceramic member 22).

The kneading of the mixture can be performed by the same method and under the same conditions as described above in connection with the titanium molded body composition.

The ceramic molded body 22' (a non-sintered body of the ceramic member 22) is obtained by molding the ceramic molded body composition through use of a required molding method. Although the molding method of the ceramic molded body 22' is not particularly limited to a specific method, an injection molding method is generally used because the ceramic molded body 22' to be molded has a small size and a complex shape.

At the end of the injection molding process, the molded body thus obtained may be subjected to machining, laser processing, etching and so forth in order to remove burrs or to form a minute structure such as a groove or the like.

The molded body obtained by use of the ceramic molded body composition contains the binder in a relatively high content percentage. Therefore, the molded body is easier to process than the ceramic degreased body 22" and the ceramic sintered body (the ceramic member 22) which will be set forth below. This means that the molded body can be easily subjected to the above processing.

Assembling Step

Next, the titanium molded body 21' and the ceramic molded body 22' obtained in the above manner are assembled together to obtain an assembled body (see FIG. 3C).

In the present step, the titanium molded body 21' and the ceramic molded body 22' are assembled together by inserting the protrusion 212' of the titanium molded body 21' (corresponding to the protrusion 212 of the titanium member 21) into the recess 222' of the ceramic molded body 22' (corresponding to the recess 222 of the ceramic member 22) as illustrated in FIG. 4A.

A clearance with a sufficiently great width exists between the protrusion (a non-contracted protrusion) 212' of the titanium molded body 21' and the recess (a non-contracted recess) 222' of the ceramic molded body 22'. This reliably prevents the titanium molded body 21' and the ceramic molded body 22' from undergoing inadvertent deformation, e.g., when the protrusion 212' is inserted into the recess 222'.

Degreasing Step

Next, the assembled body formed of the titanium molded body 21' and the ceramic molded body 22' is subjected to a degreasing process. By doing so, the binder contained in the titanium molded body 21' is removed therefrom to transform the titanium molded body 21' into a titanium degreased body 21", and the binder contained in the ceramic molded body 22' is removed therefrom to transform the ceramic molded body 22' into a ceramic degreased body 22" (see FIG. 3D).

A method for the degreasing process is not particularly limited to a specific method. Examples of the method for the degreasing process include a heat treatment either in a non-oxidant atmosphere, e.g., in a vacuum or depressurized state (of, e.g., $1 \times 10^{-1}$ to $1 \times 10^{-6}$ Torr or 13.3 to $1.33 \times 10^{-4}$ Pa) or under the presence of a gas such as a nitrogen gas, an argon gas and the like.

A processing temperature in the degreasing (heat treatment) step is not particularly limited to a specific value, but is preferably in the range of 100 to 780° C., and more preferably in the range of 150 to 720° C.

Further, a processing (heat treatment) time in the degreasing (heat treatment) step is not particularly limited to a specific value, but is preferably in the range of 0.5 to 20 hours, and more preferably in the range of 1 to 10 hours.

In this regard, it is to be noted that the degreasing process using the heat treatment may be performed through a plurality of steps for different purposes (e.g., for the purpose of shortening the degreasing time).

In this case, it may be possible to use, e.g., a method by which a former half of the degreasing process is performed at a low temperature and a latter half of the degreasing process is performed at a high temperature, a method by which a low-temperature degreasing process and a high-temperature degreasing process are performed alternately, or the like.

In the case where the titanium molded body 21' and the ceramic molded body 22' are composed of different materials containing different binders from each other, it may be possible to perform a first degreasing process in such a condition that the binder is preferentially removed from one molded body (the molded body containing a binder removable at a lower temperature) and then perform a second degreasing process in such a condition that the binder is preferentially removed from the other molded body (the molded body containing a binder removable at a higher temperature).

At the end of the degreasing process, the assembled body including the titanium degreased body 21" and the ceramic degreased body 22" may be subjected to machining, electric discharging, laser processing, etching and so forth in order to remove burrs or to form a minute structure such as a groove or the like.

The degreased bodies (the titanium degreased body 21" and the ceramic degreased body 22") are easier to process than the sintered bodies (the titanium member 21 and the ceramic member 22).

In this regard, it is to be noted that the binders contained in the molded bodies (the titanium molded body 21' and the ceramic molded body 22') may not be completely removed therefrom in this step. In this case, it is possible to suitably remove the residual binders in the following sintering step.

Sintering Step

Next, the assembled body thus degreased is subjected to a sintering process, whereby the titanium degreased body 21" (a non-sintered body of the titanium member 21) is transformed into the titanium member (sintered body) 21 and the ceramic degreased body 22" (a non-sintered body of the ceramic member 22) is transformed into the ceramic member (sintered body) 22.

Thus, the titanium member 21 is firmly fixed and joined to the ceramic member 22 (see FIG. 3E). This provides the abutment 2 in which the titanium member 21 and the ceramic member 22 are fixedly joined together.

As described above, one of the features of the present invention resides in that the titanium member is firmly fixed and joined to the ceramic member by subjecting the assembled body consisting of the titanium molded body and the ceramic molded body to the degreasing process and the sintering process.

Alternatively, it would be conceivable that a ceramic member and a titanium member are independently produced and bonded together by use of, e.g., dental cement. However, in general, titanium or titanium alloy exhibits inferior bondability (adhesiveness) with respect to ceramic. Therefore, if the ceramic member and the titanium member are merely bonded together by the use of the dental cement, it is impossible to attain sufficiently high bonding strength. It is also likely that a dental implant is destroyed after its application to a living body.

As a further alternative, it would be conceivable that an adhesive agent stronger than the generally available dental cement is used in bonding a ceramic member and a titanium member together. In this case, however, there exists a hazard that a component contained in the adhesive agent may adversely affect the living body to which a dental implant is applied.

The titanium member 21 and the ceramic member 22 are formed due to contraction of the molded bodies through the degreasing process and the sintering process. As a result of this contraction, the protrusion (a contracted protrusion) 212 of the titanium member 21 is in close contact with and fitted to the recess (a contracted recess) 222 of the ceramic member 22.

In other words, a clearance that has existed between the titanium molded body 21' (the protrusion 212') and the ceramic molded body 22' (the recess 222') in the assembling process thereof is eliminated by degreasing and sintering the titanium molded body 21' and the ceramic molded body 22', thereby bringing the titanium member 21 into close contact with the ceramic member 22.

Consequently, the titanium member 21 is firmly fixed to the ceramic member 22 so that the titanium member 21 and the ceramic member 22 can be kept in an inseparable state.

Particularly, the titanium molded body 21' used in the present embodiment has the cross-sectional area increasing portion 213' set forth above and the resultant titanium member 21 has the cross-sectional area increasing portion 213.

Therefore, even if a relatively great tensile force is imparted in a direction parallel to a direction of depth of the recess 222 (a direction of a height of the protrusion 212), it is possible to keep the titanium member 21 and the ceramic member 22 in a fixedly coupled state.

In addition, if the content percentage of the binder contained in the titanium molded body 21' (the molded body having the protrusion) and the content percentage of the binder contained in the ceramic molded body 22' (the molded body having the recess) are set to satisfy the relation mentioned earlier, the titanium member 21 is more firmly fixed and joined to the ceramic member 22, thereby increasing mechanical stability of the dental implant.

In the present embodiment, the following effects are attained because the titanium molded body 21' has the protrusion 212' and the ceramic molded body 22' has the recess 222'.

In general, oxide-based ceramic of which the ceramic molded body 22' is composed has a melting point higher than that of titanium or titanium alloy. For this reason, the ceramic member 22 (the ceramic degreased body 22") is less deformable than the titanium member 21 (the titanium degreased body 21") in the sintering step, while the titanium member 21 (the titanium degreased body 21") undergoes suitable deformation.

The protrusion 212 of the titanium member 21 conforms in shape to the recess 222 of the ceramic member 22, whereby adhesion between the protrusion 212 and the recess 222 grows extremely high. This greatly improves mechanical stability of the dental implant (the abutment 2) obtained.

Although the titanium member 21 is more easily deformed than the ceramic member 22 in the sintering step, it is possible to reliably prevent the titanium member 21 from undergoing any involuntary deformation in the temperature range described above.

A method for the sintering process is not particularly limited to a specific method. Examples of the method for the sintering process include a heat treatment either in a non-oxidant atmosphere, e.g., in a vacuum or depressurized state (of, e.g., $1\times10^{-2}$ to $1\times10^{-6}$ Torr or 133 to $1.33\times10^{-4}$ Pa) or under the presence of a gas such as a nitrogen gas, an argon gas and the like.

The atmosphere in which the sintering step is performed may be changed in the midst of the step. For example, the sintering atmosphere may be a depressurized atmosphere at the outset and may be changed to an inert atmosphere in the middle of the sintering step.

Furthermore, the sintering step may be divided into two or more steps. This makes it possible to improve sintering efficiency and to shorten a sintering time.

It is preferred that the sintering step is performed just after the degreasing step. This allows the degreasing step to serve as a pre-sintering step in which the degreased bodies (the titanium degreased body 21" and the ceramic degreased body 22") are pre-heated. This ensures that the degreased bodies are sintered in a reliable manner.

A processing temperature in the sintering (heat treatment) step is not particularly limited to a specific value, but is preferably in the range of 1000 to 1500° C., and more preferably in the range of 1050 to 1450° C.

If the processing temperature falls within the above-noted range, it is possible to prevent any inadvertent deformation during the sintering step and also to reliably obtain an abutment 2 in which the titanium member 21 and the ceramic member 22 are more firmly fixed and joined together.

A processing (heat treatment) time in the sintering (heat treatment) step is preferably in the range of 0.5 to 20 hours, and more preferably in the range of 1 to 15 hours.

In this regard, it is to be noted that the degreasing process using the heat treatment may be performed through a plurality of steps for different purposes (e.g., for the purpose of shortening the sintering time).

In this case, it may be possible to use, e.g., a method by which a former half of the sintering process is performed at a low temperature and a latter half of the sintering process is performed at a high temperature or a method by which a low-temperature sintering process and a high-temperature sintering process are performed alternately.

At the end of the sintering process, the sintered bodies thus obtained may be subjected to machining, electric discharging, laser processing, etching and so forth in order to remove burrs or to form a minute structure such as a groove or the like.

As compared to the molded bodies (the titanium molded body 21' and the ceramic molded body 22') and the degreased bodies (the titanium degreased body 21" and the ceramic degreased body 22"), the sintered bodies are closer in shape and size to the members to be produced (the titanium member 21 and the ceramic member 22).

This means that dimensional accuracy of the abutment (the titanium member 21 and the ceramic member 22) finally obtained by processing the sintered bodies is greater than that of the abutment 2 produced by subjecting the molded bodies or the degreased bodies to machining, electric discharging, laser processing, etching and so forth.

Production of Fixture

The fixture 1 is produced independently of the production of the abutment 2. A method of producing the fixture 1 is not particularly limited to a specific method.

It is preferred that the fixture 1 is produced by a method which includes a molding step (a molded fixture body production step) for molding a molded body composition containing powder composed of a constituent material of the fixture 1 and a binder to obtain a molded fixture body, a degreasing step (a molded fixture body degreasing step) for degreasing the molded fixture body by removing the binder contained in the molded fixture body therefrom to transform it into a degreased fixture body, and a sintering step (a degreased fixture body sintering step) for sintering the degreased fixture body.

Use of this method makes it possible to easily and accurately produce the fixture 1 even if the fixture 1 is of the type used in the dental implant 10 having a minute structure. In the case where the fixture 1 is produced by the above method, it is possible to produce the molded fixture body in the same manner as available in molding the titanium molded body described earlier.

Furthermore, the degreasing process and the subsequent sintering process for the molded fixture body can be performed by the same method and in the same conditions as described above with regard to the degreasing step (for the assembled body) and the sintering step (for the assembled body).

The dental implant 10 is obtained by producing the fixture 1 and the abutment 2 in the above-described manner (see FIG. 3F).

While a preferred embodiment of the present invention has been described above, the present invention is not limited thereto. For example, an arbitrary step may be optionally added to the method of manufacturing the dental implant (particularly, the abutment).

Furthermore, although the dental implant includes the fixture and the abutment in the embodiment described above, it may have other structures as long as the titanium member and the ceramic member are fixed together in the above-mentioned manner. As an example, the dental implant of the present invention may be comprised of only the titanium member and the ceramic member.

Moreover, although the titanium molded body (the titanium member) has the protrusion and the ceramic molded body (the ceramic member) has the recess in the embodiment described above, the titanium molded body (the titanium member) may be modified to have a recess and the ceramic molded body (the ceramic member) may be modified to have a protrusion.

Furthermore, at least one of the titanium molded body (the titanium member) and the ceramic molded body (the ceramic member) may not be provided with the protrusion or the recess. In addition, although the abutment is comprised of two members in the embodiment described above, it may include three or more members.

EXAMPLES

Next, description will be made on specific examples of the present invention.

1. Manufacture of Dental Implant

Example 1

1-1. Production of Fixture

Prepared first was titanium powder with an average particle size of 20 μm, which was produced by a gas atomizing method.

A binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of the titanium powder to obtain a mixture.

The mixture was kneaded by a pressure type kneader (kneading machine) under the conditions of a kneading temperature of 100° C. and a kneading time of 60 min to obtain a kneaded product. This kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of the fixture to be produced under the molding conditions of a material temperature of 130° C. and an injection pressure of 10.8 MPa (110 kgf/cm$^2$) to obtain a molded fixture body within the mold. Thereafter, the molded fixture body was ejected from the mold. This process was repeatedly performed to obtain a specified number of the molded fixture bodies.

The molded fixture bodies thus obtained were degreased under the conditions of a degreasing temperature of 450° C., a degreasing time of one hour and a degreasing atmosphere of nitrogen gas (set to the atmospheric pressure), so that the binder contained in the molded fixture bodies was removed therefrom to transform them into degreased fixture bodies.

Then, under the conditions of a sintering temperature of 1200° C., a sintering time of three hours and a vacuum sintering atmosphere, the degreased fixture bodies were sintered to obtain sintered bodies.

Subsequently, the sintered bodies thus obtained were machined so that cutout portions (see FIG. 1A) were formed to produce fixtures as desired.

1-2. Production of Abutment

Titanium Molded Body Production Step

Prepared first was titanium powder with an average particle size of 20 μm, which was produced by a gas atomizing method.

A binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of the titanium powder to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 5 mm. The pellets were put into an injection molding machine, and injected into a mold provided in the machine and having an internal shape corresponding to an external shape of the titanium member to be produced under the molding conditions of a material temperature of 130° C. and an injection pressure of 10.8 MPa (110 kgf/cm$^2$) to obtain a titanium molded body within the mold. At this time, the protrusion was formed in the titanium molded body. Thereafter, the titanium molded body having the protrusion was ejected from the mold. This process was repeatedly performed to obtain a specified number of the titanium molded bodies (see FIG. 3A).

Further, the titanium molded bodies thus obtained had the same composition ratio as that of the mixture (the composition) prepared at the outset.

Each of the titanium molded bodies obtained in this manner had a protrusion whose cross-sectional shape was non-circular (rectangular). Furthermore, each of the titanium molded bodies had a cross-sectional area increasing portion extending over a full heightwise length of the protrusion.

An angle θ between a surface (circumference surface) of the cross-sectional area increasing portion and a heightwise axis of the protrusion was 1.5°.

Ceramic Molded Body Production Step

Prepared first was zirconia powder with an average particle size of 0.5 μm, which was produced by a co-precipitation method.

A binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of the zirconia powder to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of the ceramic member to be produced under the molding conditions of a material temperature of 140° C. and an injection pressure of 10.8 MPa (110 kgf/cm$^2$) to obtain a ceramic molded body within the mold. At this time, the recess was formed in the ceramic molded body. Thereafter, the ceramic molded body having the recess was ejected from the mold. This process was repeatedly performed to obtain a specified number of the ceramic molded bodies (see FIG. 3B).

Further, the ceramic molded bodies thus obtained had the same composition ratio as that of the mixture (the composition) prepared at the outset.

Assembling Step

Next, the titanium molded bodies and the ceramic molded bodies thus obtained were assembled together to obtain assembled bodies (see FIG. 3C). At this time, the protrusion of each of the titanium molded bodies was inserted into the recess of each of the ceramic molded bodies.

Degreasing Step

Next, the assembled bodies thus obtained were degreased under the conditions of a degreasing temperature of 450° C., a degreasing time of two hours and a degreasing atmosphere of nitrogen gas (set to the atmospheric pressure).

By doing so, the binder contained in the titanium molded bodies was removed therefrom to transform them into titanium degreased bodies, and the binder contained in the ceramic molded bodies was removed therefrom to transform them into ceramic degreased bodies (see FIG. 3D).

Sintering Step

Next, the titanium degreased bodies and the ceramic degreased bodies thus obtained were sintered under the conditions of a sintering temperature of 1400° C., a sintering time of five hours and a sintering atmosphere of argon gas (set to the atmospheric pressure).

By doing so, the titanium degreased bodies were transformed into titanium members as sintered bodies, and the ceramic degreased bodies were transformed into ceramic members as sintered bodies. Thus, the titanium members were firmly fixed and joined to the ceramic members (see FIG. 3E).

Machining Step

Subsequently, the abutments as desired were obtained by machining the titanium members and adjusting a shape of each of male thread portions thereof. In the abutments thus obtained, the recess of each of the ceramic members was fitted to the protrusion of each of the titanium members so that the titanium members and the ceramic members could be strongly fixed and joined together.

Finally, dental implants were obtained by combining the fixtures and the abutments produced as above.

Examples 2 to 7

Dental implants were manufactured in the same manner as in Example 1, except that the composition ratio of the composition (the kneaded product) used in producing the abutments (the titanium members and the ceramic members) was changed, that the same composition as that of the titanium molded bodies was used as the composition (the kneaded product) for production of the fixtures, and that the production conditions of the abutments were changed as shown in Table 1.

Comparative Example 1

Dental implants were manufactured in the same manner as in Example 1, except that each of the abutments was produced in the form of an integral titanium member having the same external shape as that of each of the abutments produced in the foregoing examples.

Hereinbelow, an abutment production method according to this comparative example will be described in detail.

First, a binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of titanium powder having an average particle size of 20 μm, which was produced by a gas atomizing method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 5 mm. The pellets were put into an injection molding machine, and injected into a mold provided in the machine and having an internal shape corresponding to an external shape of the abutment to be produced under the molding conditions of a material temperature of 130° C. and an injection pressure of 10.8 MPa (110 kgf/cm$^2$) to obtain a molded body within the mold. Thereafter, the molded body was ejected from the mold. This process was repeatedly performed to obtain a specified number of the molded bodies.

In this regard, it is to be noted that at this time, a size of each of the molded bodies was decided by taking into account shrinkage thereof which would occur in the subsequent degreasing and sintering steps.

Next, the molded bodies thus obtained were degreased under the conditions of a degreasing temperature of 450° C., a degreasing time of one hour and a degreasing atmosphere of nitrogen gas (set to the atmospheric pressure). By doing so, the binder contained in the molded bodies was removed therefrom to transform them into degreased bodies.

Then, the degreased bodies were sintered under the conditions of a sintering temperature of 1200° C., a sintering time of three hours and a sintering atmosphere of argon gas (set to the atmospheric pressure) to obtain sintered bodies.

Subsequently, the abutments as desired were obtained by machining the sintered bodies and adjusting a shape of each of male thread portions thereof.

Comparative Example 2

Dental implants were manufactured in the same manner as in Example 1, except that each of the abutments was produced in the form of an integral zirconia member having the same external shape as that of each of the abutments produced in the foregoing examples.

Hereinbelow, an abutment production method according to this comparative example will be described in detail.

First, a binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of zirconia powder having an average particle size of 0.5 µm, which was produced by a co-precipitation method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of the abutment to be produced under the molding conditions of a material temperature of 140° C. and an injection pressure of 10.8 MPa (110 kgf/cm$^2$) to obtain a molded body within the mold. Thereafter, the molded body was ejected from the mold. This process was repeatedly performed to obtain a specified number of the molded bodies.

In this regard, it is to be noted that at this time, a size of each of the molded bodies was decided by taking into account shrinkage which would occur in the subsequent degreasing and sintering steps.

Next, the molded bodies thus obtained were degreased under the conditions of a degreasing temperature of 500° C., a degreasing time of two hours and a degreasing atmosphere of nitrogen gas (set to the atmospheric pressure). By doing so, the binder contained in the molded bodies was removed therefrom to transform them into degreased bodies.

Then, the degreased bodies were sintered under the conditions of a sintering temperature of 1450° C., a sintering time of three hours and a sintering atmosphere of air to obtain sintered bodies.

Subsequently, the abutments as desired were obtained by machining the sintered bodies and adjusting a shape of each of male thread portions thereof.

Comparative Example 3

Dental implants were manufactured in the same manner as in Example 1, except that each of the abutments was produced by independently producing and bonding titanium members (titanium sintered bodies) and ceramic members (ceramic sintered bodies) with dental cement.

In this regard, it is to be noted that each of the abutments had the same external shape as that of each of the abutments produced in the foregoing examples.

Hereinbelow, an abutment production method according to this comparative example will be described in detail.

Production of Titanium Members

First, a binder composed of 2.7 wt % of polystyrene (PS), 2.7 wt % of ethylene-vinyl acetate copolymer (EVA) and 2.3 wt % of paraffin wax and 1.3 wt % of dibutylphthalate (plasticizer) were mixed with 91 wt % of titanium powder having an average particle size of 20 µm, which was produced by a gas atomizing method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Figure 5:
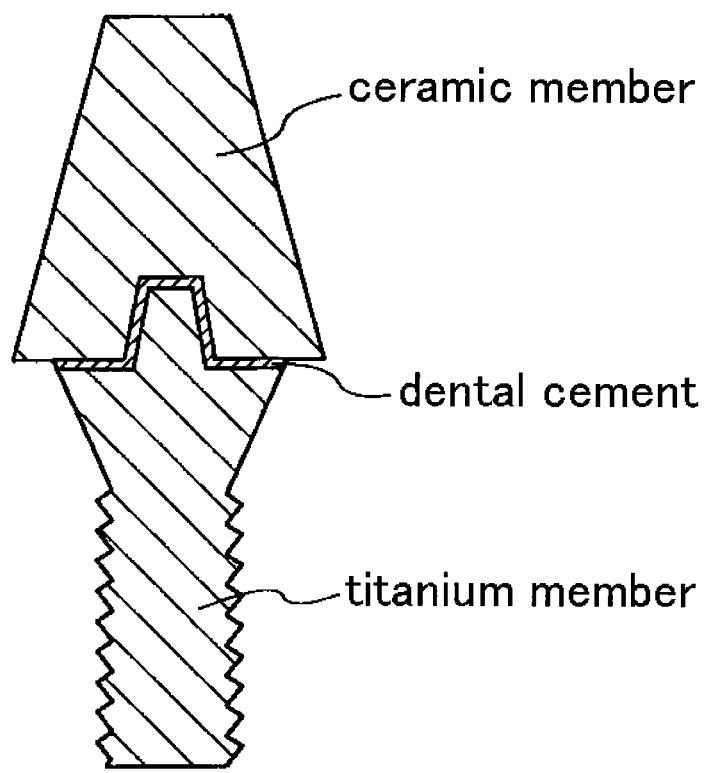
FIG. 5 is a vertical section view showing an abutment manufactured in Comparative Example 3.

Next, the kneaded product was pulverized into pellets with an average particle size of 5 mm. The pellets were put into an injection molding machine, and injected into a mold provided in the machine and having an internal shape corresponding to an external shape of a lower part of an abutment shown in FIG. 5 (a member to be threadedly coupled to the fixture) under the molding conditions of a material temperature of 130° C. and an injection pressure of 10.8 MPa (110 kgf/cm$^2$) to obtain a titanium molded body within the mold. Thereafter, the titanium molded body was ejected from the mold. This process was repeatedly performed to obtain a specified number of the titanium molded bodies.

In this regard, it is to be noted that at this time, a size of each of the titanium molded bodies was decided by taking into account shrinkage which would occur in the subsequent degreasing and sintering steps.

Next, the titanium molded bodies thus obtained were degreased under the conditions of a degreasing temperature of 450° C., a degreasing time of one hour and a degreasing atmosphere of nitrogen gas (set to the atmospheric pressure). By doing so, the binder contained in the titanium molded bodies was removed therefrom to transform them into titanium degreased bodies.

Then, the titanium degreased bodies were sintered under the conditions of a sintering temperature of 1200° C., a sintering time of three hours and a sintering atmosphere of argon gas (set to the atmospheric pressure) to obtain titanium sintered bodies.

Subsequently, the titanium members as desired were obtained by machining the titanium sintered bodies and adjusting a shape of each of male thread portions thereof.

Production of Ceramic Members

First, a binder composed of 4.8 wt % of polystyrene (PS), 3.8 wt % of ethylene-vinyl acetate copolymer (EVA) and 4.8 wt % of paraffin wax and 2.6 wt % of dibutylphthalate (plasticizer) were mixed with 84 wt % of zirconia powder having an average particle size of 0.5 µm, which was produced by a co-precipitation method, to obtain a mixture.

The mixture was kneaded by a pressure type kneader (kneading machine) under the conditions of a kneading temperature of 100° C. and a kneading time of 60 min to obtain a kneaded product. The kneading was carried out in a nitrogen atmosphere.

Next, the kneaded product was pulverized into pellets with an average particle size of 3 mm. The pellets were put into an injection molding machine, and injected into a mold provided in the machine and having an internal shape corresponding to an external shape of an upper part of an abutment shown in FIG. 5 (a member to be capped by a crown restoration) under the molding conditions of a material temperature of 140° C. and an injection pressure of 10.8 MPa (110 kgf/cm$^2$) to obtain a ceramic molded body within the mold. Thereafter, the ceramic molded body was ejected from the mold. This process was repeatedly performed to obtain a specified number of the ceramic molded bodies.

In this regard, it is to be noted that at this time, a size of each of the ceramic molded bodies was decided by taking into account shrinkage which would occur in the subsequent degreasing and sintering steps.

Next, the ceramic molded bodies thus obtained were degreased under the conditions of a degreasing temperature of 500° C., a degreasing time of two hours and a degreasing atmosphere of nitrogen gas (set to the atmospheric pressure). By doing so, the binder contained in the ceramic molded bodies was removed therefrom to transform them into ceramic degreased bodies.

Then, the ceramic degreased bodies were sintered under the conditions of a sintering temperature of 1450° C., a sintering time of three hours and a sintering atmosphere of argon gas (set to the atmospheric pressure) to obtain ceramic members.

Bonding of Titanium Members and Ceramic Members (Completion of Abutments)

Subsequently, abutments were produced by bonding the titanium members (the titanium sintered bodies) and the ceramic members (the ceramic sintered bodies) with dental cement ("Glass Ionomer", produced by GC America, Inc.).

The production conditions of the fixtures and the abutments employed in the respective examples and the respective comparative examples are collectively shown in Table 1. The configurations of the dental implants manufactured in the respective examples and the respective comparative examples are collectively shown in Table 2.

The symbol θ in Table 1 refers to the angle between the surface of the cross-sectional area increasing portion of the titanium molded body and the heightwise axis of the protrusion of the titanium molded body.

The symbol θ in Table 2 refers to the angle between the surface of the cross-sectional area increasing portion of the titanium member and the heightwise axis of the protrusion of the titanium member.

Referring to Comparative Example 3 shown in Table 1, the processing conditions adopted in the degreasing step for the titanium molded bodies are indicated in the upper line of the degreasing step column, and the processing conditions adopted in the degreasing step for the ceramic molded bodies are indicated in the lower line of the degreasing step column.

Further, the processing conditions adopted in the sintering step for the titanium degreased bodies are indicated in the upper line of the sintering step column, and the processing conditions adopted in the sintering step for the ceramic degreased bodies are indicated in the lower line of the sintering step column.

Referring to Comparative Examples 1 and 2 shown in Table 2, the conditions for the portion threadedly coupled to the fixture (the portion corresponding to the titanium member in the present invention) are indicated in the titanium member column, and the conditions for the portion capped by the crown restoration (the portion corresponding to the ceramic member in the present invention) are indicated in the ceramic member column.

TABLE 1

| | Ceramic Molded Body Production Step | | | | Titanium Molded Body Production Step | | | | | | | |
|---|---|---|---|---|---|---|---|---|---|---|---|---|
| | Ceramic Molded Body | | | | Titanium Molded Body | | | | | | | |
| | | | Content Percentage [wt %] | | | | Content Percentage [wt %] | | | Protrusion | | Existence or Non-existence |
| | Material Temperature [° C.] | Injection Pressure [MPa] | Powder | Binder ($C_A$) | Material Temperature [° C.] | Injection Pressure [MPa] | Powder | Binder ($C_B$) | Height [mm] | Cross-sectional Shape | of Cross-sectional Area Increasing Portion | θ [°] |
| Ex. 1 | 140 | 10.8 | 84 | 13.4 | 130 | 10.8 | 91 | 7.7 | 4 | Rectangle | Existence | 1.5 |
| Ex. 2 | 140 | 10.8 | 84 | 13.4 | 130 | 10.8 | 91 | 7.7 | 4 | Rectangle | Existence | 1 |
| Ex. 3 | 140 | 10.8 | 84 | 13.4 | 130 | 10.8 | 91 | 7.7 | 2 | Ellipsoid | Existence | 4 |
| Ex. 4 | 140 | 10.8 | 84 | 13.4 | 130 | 10.8 | 91 | 7.7 | 5 | Ellipsoid | Existence | 1.5 |
| Ex. 5 | 140 | 10.8 | 87 | 10.7 | 130 | 10.8 | 91 | 7.7 | 4 | Rectangle | Existence | 1.5 |
| Ex. 6 | 140 | 10.8 | 77 | 19.2 | 130 | 10.8 | 95 | 4.2 | 4 | Rectangle | Existence | 1.5 |
| Ex. 7 | 140 | 10.8 | 60 | 33.6 | 130 | 10.8 | 65 | 29.4 | 4 | Rectangle | Existence | 1.5 |
| Com. Ex. 1 | — | — | — | — | 130 | 10.8 | 91 | 7.7 | — | — | Non-existence | — |
| Com. Ex. 2 | 140 | 10.8 | 84 | 13.4 | — | — | — | — | — | — | Non-existence | — |
| Com. Ex. 3 | 140 | 10.8 | 84 | 13.4 | 130 | 10.8 | 91 | 7.7 | — | — | Non-existence | — |

| | $C_A - C_B$ [wt %] | Assembling Step Existence or Non-existence of This Step | Degreasing Step Processing Temperature [° C.] | Processing Time [hours] | Atmosphere | Sintering Step Processing Temperature [° C.] | Processing Time [hours] | Atmosphere | Machining Step Existence or Non-existence of This Step |
|---|---|---|---|---|---|---|---|---|---|
| Ex. 1 | 5.7 | Existence | 450 | 2 | $N_2$ | 1400 | 5 | Ar | Existence |
| Ex. 2 | 5.7 | Existence | 450 | 2 | $N_2$ | 1400 | 5 | Ar | Existence |
| Ex. 3 | 5.7 | Existence | 450 | 2 | $N_2$ | 1400 | 5 | Ar | Existence |
| Ex. 4 | 5.7 | Existence | 450 | 2 | $N_2$ | 1400 | 5 | Ar | Existence |
| Ex. 5 | 3.0 | Existence | 450 | 2 | $N_2$ | 1400 | 5 | Ar | Existence |
| Ex. 6 | 15.0 | Existence | 450 | 2 | $N_2$ | 1400 | 5 | Ar | Existence |
| Ex. 7 | 4.2 | Existence | 450 | 2 | $N_2$ | 1400 | 5 | Ar | Existence |
| Com. Ex. 1 | — | Non-existence | 450 | 1 | $N_2$ | 1200 | 3 | Ar | Existence |

TABLE 1-continued

| | | | | | | | | | |
|---|---|---|---|---|---|---|---|---|---|
| Com. Ex. 2 | — | Non-existence | 500 | 2 | N$_2$ | 1450 | 3 | Air | Existence |
| Com. Ex. 3 | — | Non-existence | 450 | 1 | N$_2$ | 1200 | 3 | Ar | Existence |
| | | | 500 | 2 | N$_2$ | 1450 | 3 | Ar | Existence |

TABLE 2

| | Configuration of Abutment | | | | | Configuration of Fixture | |
|---|---|---|---|---|---|---|---|
| | Ceramic Member | | Titanium Member | | | | |
| | Constituent Material | Depth of Recess [mm] | Constituent Material | Height of Protrusion [mm] | Existence or Non-existence of Cross-sectional Area Increasing Portion | θ [°] | Constituent Material | Existence or Non-existence of Cutout Portion |
| Ex. 1 | ZrO$_2$ | 4.2 | Ti | 4 | Existence | 1.5 | Ti | Existence |
| Ex. 2 | ZrO$_2$ | 4.2 | Ti | 4 | Existence | 1 | Ti | Existence |
| Ex. 3 | ZrO$_2$ | 2.1 | Ti | 2 | Existence | 4 | Ti | Existence |
| Ex. 4 | ZrO$_2$ | 5.2 | Ti | 5 | Existence | 1.5 | Ti | Existence |
| Ex. 5 | ZrO$_2$ | 4.2 | Ti | 4 | Existence | 1.5 | Ti | Existence |
| Ex. 6 | ZrO$_2$ | 4.2 | Ti | 4 | Existence | 1.5 | Ti | Existence |
| Ex. 7 | ZrO$_2$ | 4.2 | Ti | 4 | Existence | 1.5 | Ti | Existence |
| Com. Ex. 1 | Ti | — | Ti | — | — | — | Ti | Existence |
| Com. Ex. 2 | ZrO$_2$ | — | ZrO$_2$ | — | — | — | Ti | Existence |
| Com. Ex. 3 | ZrO$_2$ | 4.2 | Ti | 4 | Non-existence | — | Ti | Existence |

2. Bonding of Crown Restoration

In a state that the fixture and the abutment of the dental implant obtained in each of the examples had been threadedly coupled together, a crown restoration was bonded by dental cement ("Superbond", produced by Sun Medical Ltd.) to a surface (a metal bonding surface shown in FIGS. 1A to 1C) of the abutment opposite to a side on which the abutment was threadedly coupled to the fixture.

The crown restoration used was of a type including a metal layer made of gold and arranged on an inner surface side (a surface facing the abutment) and a ceramic portion made of silicon oxide (silica) and aluminum oxide (alumina) and arranged on an outer surface side (a surface opposite to the abutment). Thereafter, the crown restoration was fixed to the dental implant by hardening the dental cement.

With respect to the dental implant obtained in each of the comparative examples, a crown restoration was bonded by dental cement ("Superbond", produced by Sun Medical Ltd.) to a portion corresponding to the metal bonding surface of the abutment obtained in each of the examples. Then, the dental cement was hardened.

3. Evaluation 3-1. Measurement of Elution Amount of Metal Ions

In respect of each of the dental implants of the examples and the comparative examples to which the crown restorations were bonded in the above manner, an elution amount of metal ions was found by the following method.

The abutments to which the crown restorations were bonded were immersed in 80 mL of 1 wt % latic acid solution for three months. Thereafter, the elution amount of titanium in the solution was analyzed by a plasma emission spectroscopy device.

3-2. Measurement of Fixing Strength

In respect of each of the dental implants of the examples and the comparative examples to which the crown restorations were bonded in the above manner (which dental implants were different from the dental implants used in Section 3-1 for measuring the elution amount of metal ions), fixing strength (bonding strength) between the titanium member and the ceramic member was found in the following method.

Figure 6:
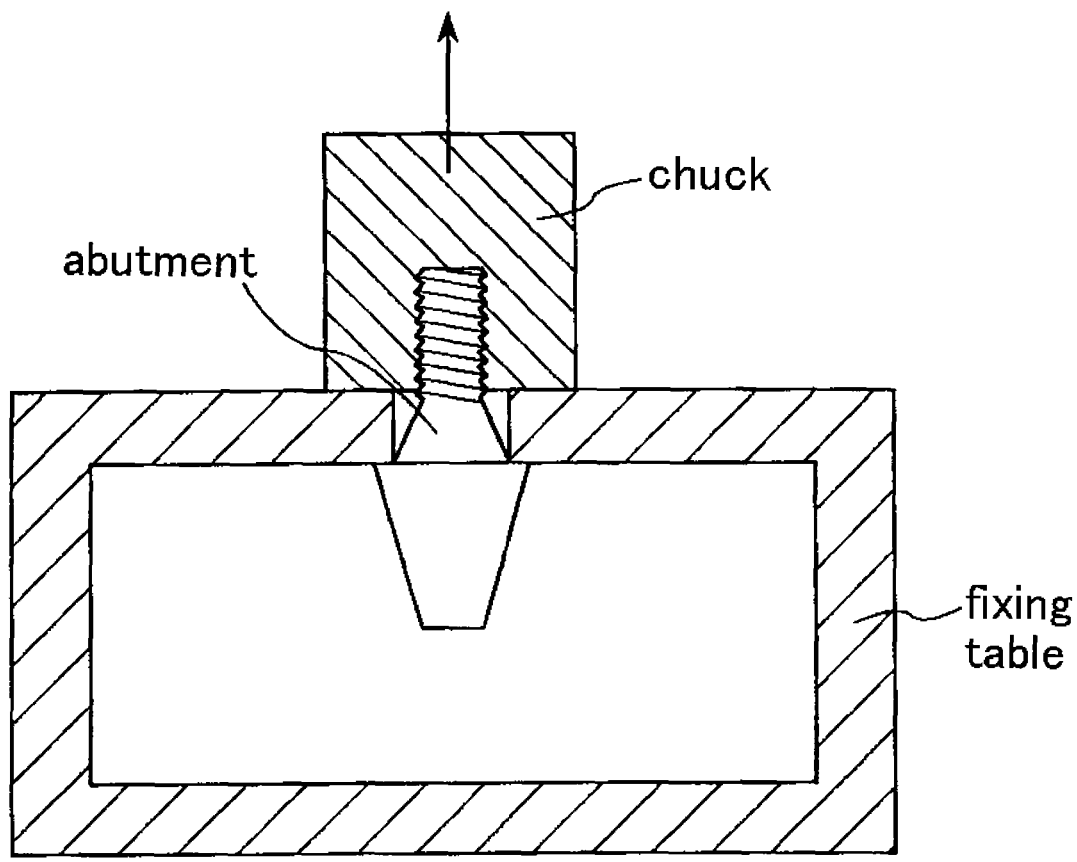
FIG. 6 is a view schematically illustrating a configuration of a jig used in measuring fixing strength and also explaining a method of measuring the fixing strength.

Using a jig as shown in FIG. 6, the abutment was attached to a fixing table and a chuck was mounted to the male thread portion of the abutment. Then, the chuck was mounted to a tensile tester and a strength test was conducted by a drawing method.

3-3. Drop Test

In respect of each of the dental implants of the examples and the comparative examples to which the crown restorations were bonded in the above manner (which dental implants were different from the dental implants used in measuring the elution amount of metal ions in Section 3-1 and the dental implants used in measuring the fixing strength in Section 3-2), a drop test was carried out in the following method.

The dental implants of the examples and the comparative examples to which the crown restorations were bonded (ten dental implants of the examples and ten dental implants of the comparative examples) were dropped one hundred times from a 2 m-high position onto a 2 cm-thick stainless steel plate.

External appearance of each of the dental implants thus dropped was visually observed and evaluated according to the following four criteria.

A: Cracks or defects were not recognized at all in the dental implants.

B: Tiny cracks or defects were recognized in one to five dental implants.

C: Noticeable cracks or defects were recognized in one to five dental implants, or tiny cracks or defects were recognized in six to ten dental implants.

D: Noticeable cracks or defects were recognized in six to ten dental implants.

Results of these evaluations were collectively shown in Table 3.

TABLE 3

| | Elution Amount of Metal Ions [ppm] | Fixing Strength [MPa] | Drop Test |
|---|---|---|---|
| Ex. 1 | 0.6 | 24 | A |
| Ex. 2 | 0.7 | 22 | A |
| Ex. 3 | 0.7 | 23 | A |
| Ex. 4 | 0.7 | 23 | A |
| Ex. 5 | 0.8 | 24 | A |
| Ex. 6 | 0.6 | 22 | A |
| Ex. 7 | 0.6 | 23 | A |
| Com. Ex. 1 | 12 | — | A |
| Com. Ex. 2 | 0 | — | D |
| Com. Ex. 3 | 0.7 | 11 | D |

As is apparent in Table 3, the dental implants of the present invention were all sufficiently low in the elution amount of metal ions. Furthermore, in the dental implants of the present invention, the fixing strength (joint strength) between the titanium members and the ceramic members was superior.

Moreover, the dental implants of the present invention exhibited no mismatching between themselves and the crown restorations, and no mismatching between the titanium members and the ceramic members.

In contrast, no satisfactory result was obtained in the comparative examples. More specifically, the elution amount of metal ions was exceptionally high in Comparative Example 1 in which the abutment was composed of titanium alone.

Furthermore, the mechanical strength was low and the evaluation results of drop test were quite unsatisfactory in Comparative Example 2 in which the abutment was composed of ceramic (zirconia) alone. Moreover, in case of Comparative Example 2, there was a problem in that the thread coupling between the fixture and the abutment was highly likely to be loosened.

Additionally, in case of Comparative Example 3 in which the titanium member and the ceramic member of the abutment were merely bonded by the dental cement, the bonding strength between the titanium member and the ceramic member was not sufficiently great.

Therefore, the titanium member and the ceramic member were separated from each other by a relatively weak force. Furthermore, in case of Comparative Example 3, the mechanical strength was low and the evaluation results of the drop test were quite unsatisfactory.

Further, in respect of Comparative Example 1, a quantity of the dental cement used in bonding the dental implant (the abutment) and the crown restoration was increased so that the dental implant and the crown restoration should not make direct contact with each other.

Then, the same evaluation as noted above was conducted. The results of the evaluation revealed that the bonding strength between the dental implant and the crown restoration was sharply reduced (to 9 MPa).

Furthermore, if the quantity of dental cement was increased as mentioned above, it became quite difficult, when bonding the crown restoration to the abutment, to adjust a height and angle of the crown restoration fixed to the dental implant in conformity with the design.

What is claimed is:

1. A method for manufacturing a dental implant including an abutment,
   wherein the abutment is manufactured through the steps comprising:
   molding a titanium molded body composition containing powder composed of titanium or titanium alloy and a binder to obtain a titanium molded body having a protrusion;
   molding a ceramic molded body composition containing powder composed of oxide-based ceramic and a binder to obtain a ceramic molded body having a recess, wherein the recess of the ceramic molded body has a size lager than that of the protrusion of the titanium molded body;
   assembling the titanium molded body and the ceramic molded body together to obtain an assembled body, wherein the assembled body is assembled by inserting the protrusion of the titanium molded body into the recess of the ceramic molded body so that a clearance is created therebetween;
   degreasing the assembled body so that the binder contained in the titanium molded body and the binder contained in the ceramic molded body are removed therefrom to transform the titanium molded body into a titanium degreased body and to transform the ceramic molded body into a ceramic degreased body; and
   sintering the assembled body thus degreased to transform the titanium degreased body into a titanium member as a sintered body and to transform the ceramic degreased body into a ceramic member as a sintered body so that the titanium member and the ceramic member are firmly fixed and joined together,
   wherein in the degreasing step and the sintering step, the ceramic molded body contracts to a greater degree than the titanium molded body so that the clearance is eliminated, thereby bringing the protrusion of the titanium member into close contact with, and filling, the recess of the ceramic member.

2. The method as claimed in claim 1,
   wherein a weight percentage of the binder contained in the ceramic molded body is greater than the weight percentage of the binder contained in the titanium molded body.

3. The method as claimed in claim 2, wherein the percentage of the binder contained in the titanium molded body having the protrusion is 3 wt % or more and 35 wt % or less.

4. The method as claimed in claim 2, wherein the weight percentage of the binder contained in the ceramic molded body having the recess is not less than 6 wt % binder and not or more than 40 wt % binder.

5. The method as claimed in claim 2, wherein in the case where the weight percentage of the binder contained in the ceramic molded body having the recess is denoted as $C_A$ and the weight percentage of the binder contained in the titanium molded body having the protrusion is denoted as $C_B$, the difference of $C_A$ and $C_B$ satisfy the following relation: $3\% \leq C_A - C_B \leq 15\%$.

6. The method as claimed in claim 1, wherein the end of the protrusion of the titanium molded body that is inserted into the recess of the ceramic molded body has a cross-sectional area that increases toward the base of the recess of the ceramic molded body.

7. The method as claimed in claim 1, wherein the end of the protrusion of the titanium molded body that is inserted into the recess of the ceramic molded body has a cross-sectional area that continuously increases from the start of the protrusion toward its end that faces the base of the recess of the ceramic molded body.

8. The method as claimed in claim 1, wherein the protrusion of the titanium molded body has a portion whose cross-sectional shape is non-circular.

9. The method as claimed in claim 1, wherein the ceramic member is composed of zirconia as a major component thereof.

10. The method as claimed in claim 1, wherein the dental implant further includes a fixture to be coupled to the abutment and anchored to a jawbone, and the fixture is made of titanium or titanium alloy.

11. The method as claimed in claim 1, wherein the ceramic member has a contact surface with which a metal having a composition different from that of a constituent material of the titanium member makes contact.

* * * * *